(12) United States Patent
Gijsen et al.

(10) Patent No.: US 8,193,369 B2
(45) Date of Patent: *Jun. 5, 2012

(54) BENZIMIDAZOLE CANNABINOID AGONISTS

(75) Inventors: Henricus Jacobus Maria Gijsen, Breda (BE); Michel Anna Jozef De Cleyn, Lille (BE); Michel Surkyn, Turnhout (BE)

(73) Assignee: Janssen Pharmaceutica NV, Beerse (BE)

( * ) Notice: Subject to any disclaimer, the term of this patent is extended or adjusted under 35 U.S.C. 154(b) by 164 days.

This patent is subject to a terminal disclaimer.

(21) Appl. No.: 12/593,656

(22) PCT Filed: Mar. 25, 2008

(86) PCT No.: PCT/EP2008/053480
§ 371 (c)(1),
(2), (4) Date: Sep. 29, 2009

(87) PCT Pub. No.: WO2008/119694
PCT Pub. Date: Oct. 9, 2008

(65) Prior Publication Data
US 2010/0041702 A1  Feb. 18, 2010

(30) Foreign Application Priority Data
Mar. 30, 2007  (EP) .................... 07105286

(51) Int. Cl.
| A61K 31/4184 | (2006.01) |
| A61K 31/4439 | (2006.01) |
| A61K 31/454 | (2006.01) |
| C07D 401/06 | (2006.01) |
| C07D 401/14 | (2006.01) |
| C07D 409/06 | (2006.01) |

(52) U.S. Cl. ................. 548/304.7; 546/193; 546/199; 546/273.4; 514/318; 514/322; 514/394

(58) Field of Classification Search ............... 548/304.7; 546/273.4
See application file for complete search history.

(56) References Cited

U.S. PATENT DOCUMENTS
2009/0312339 A1 * 12/2009 Gijsen et al. ............. 514/252.06

FOREIGN PATENT DOCUMENTS
| WO | WO 2005/030762 A1 | 4/2005 |
| WO | WO 2006/048754 A1 | 5/2006 |

OTHER PUBLICATIONS

Vippagunta et al. (Advanced Drug Delivery Reviews, 48 (2001), pp. 3-26.*
Souillac, et al., Characterization of Delivery Systems, Differential Scanning Calorimetry in Encyclopedia of Controlled Drug Delivery, 1999, John Wiley & Sons, pp. 212-227.*
Golub et al., Science, vol. 286, Oct. 15, 1999, pp. 531-537.*

* cited by examiner

Primary Examiner — Laura L. Stockton
(74) Attorney, Agent, or Firm — Joseph S. Kentoffio

(57) ABSTRACT

The present invention is related to novel benzimidazole compounds of Formula (I) having cannabinoid receptor agonistic properties, pharmaceutical compositions comprising these compounds, chemical processes for preparing these compounds and their use in the treatment of diseases linked to the mediation of the cannabinoid receptors in animals, in particular humans.

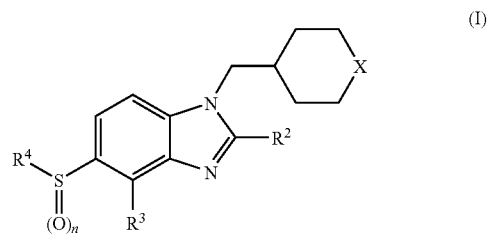

(I)

8 Claims, No Drawings

BENZIMIDAZOLE CANNABINOID AGONISTS

CROSS REFERENCE TO RELATED APPLICATIONS

This application is a national stage application of Patent Application No. PCT/EP2008/053480, filed Mar. 25, 2008, which in turn claims the benefit of EPO patent application No. 07105286.4 filed Mar. 30, 2007. The complete disclosures of the aforementioned related patent applications are hereby incorporated herein by reference for all purposes.

The present invention is related to novel benzimidazole compounds of formula (I) having selective cannabinoid receptor 2 agonistic properties, pharmaceutical compositions comprising these compounds, chemical processes for preparing these compounds and their use in the treatment of diseases linked to the mediation of the cannabinoid receptors in animals, in particular humans.

Classical cannabinoids such as the marijuana derived cannabinoid $\Delta^9$-tetrahydro-cannabinol, ($\Delta^9$-THC) produce their pharmacological effects via interaction with specific cannabinoid receptors in the body. So far, two cannabinoid receptors have been characterized: CB1, a receptor found in the mammalian brain and peripheral tissues and CB2, a receptor found predominantly in the peripheral tissues. Compounds that are agonists or antagonists for one or both of these receptors have been shown to provide a variety of pharmacological effects. There is considerable interest in developing cannabinoid analogs that have selective CB2 agonistic activity since it is believed high selectivity for CB2 receptor may offer avenues for harnessing the beneficial effect of CB receptor agonists while avoiding the central adverse events seen with cannabinoid structures (see e.g. Expert Opinion on Investigational Drugs (2005), 14(6), 695-703).

WO-2002/46168 discloses benzimidazole compounds as estrogen receptor-β ligands for use in the treatment of diseases related to the estrogen receptor-β such as Alzheimer's disease, anxiety disorders, depressive disorders, osteoporosis, cardiovascular disease, rheumatoid arthritis or prostate cancer. WO-2006/048754 discloses sulfonyl benzimidazole derivatives having CB2 agonistic activity useful in the treatment of conditions mediated by CB2 receptor activity.

The compounds of the present invention differ structurally from the cited art known compounds by the presence of a 1-piperidin-4-ylmethyl or 1-tetrahydrothiopyran-4-ylmethyl group in which the heteroatom is always substituted.

It was found the compounds of the present invention are selective CB2 agonists that unexpectedly are devoid of CB1 related side-effects such as lowering of body temperature and flat body posture compared to the art known compounds of WO-2006/048754.

The present invention relates to a compound of formula (I)

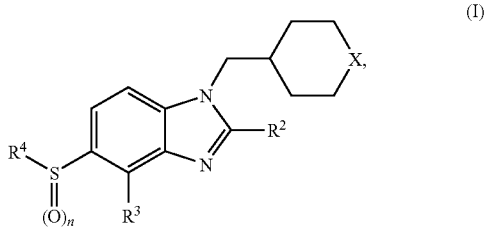

including any stereochemically isomeric form thereof, wherein
n is an integer 0, 1 or 2;
X is SO, $SO_2$ or N—(CO)—$R^1$;
$R^1$ is hydrogen;
 $C_{1-6}$alkyl;
 $C_{1-6}$alkyloxy;
 $C_{1-4}$alkyloxy$C_{1-4}$alkyl; or
 polyhalo$C_{1-6}$alkyl;
$R^2$ is $C_{1-6}$alkyl;
$R^3$ is hydrogen, halo, $C_{1-4}$alkyl, $C_{1-4}$alkyloxy, trifluoromethyl or cyano;
$R^4$ is $C_{1-8}$alkyl;
 $C_{1-8}$alkyl substituted with $C_{3-8}$cycloalkyl;
 polyhalo$C_{1-8}$alkyl;
 $C_{1-8}$alkyl substituted with 1, 2 or 3 substituents each independently selected from hydroxy, $C_{1-4}$alkyloxy, polyhalo$C_{1-4}$alkyloxy, cyano, nitro, tetrahydropyranyl, tetrahydrofuranyl, oxetanyl, aryl, or heteroaryl;
 $C_{3-8}$cycloalkyl;
 $C_{3-8}$cycloalkyl substituted with 1, 2 or 3 substituents each independently selected from hydroxy, $C_{1-4}$alkyloxy, polyhalo$C_{1-4}$alkyloxy, cyano, nitro, tetrahydropyranyl, tetrahydrofuranyl, oxetanyl, aryl, or heteroaryl;
 tetrahydropyranyl, tetrahydrofuranyl, oxetanyl aryl; or heteroaryl;
aryl is phenyl; or phenyl substituted with 1, 2 or 3 substituents each independently selected from halo, hydroxy, $C_{1-4}$alkyl, polyhalo$C_{1-4}$alkyl, $C_{1-4}$alkyloxy, polyhalo$C_{1-4}$alkyloxy, cyano, nitro, $NR^5R^6$, $R^7$-carbonyl, $R^7$—$SO_2$—, or $C_{1-4}$alkyl substituted with hydroxy, $NR^5R^6$, $R^7$-carbonyl or $R^7$—$SO_2$—;
heteroaryl is selected from furanyl, thiophenyl, pyrrolyl, pyrazolyl, imidazolyl, isoxazolyl, thiazolyl, triazolyl, tetrazolyl, isothiazolyl, thiadiazolyl, oxadiazolyl, pyridinyl, pyridazinyl, pyrimidinyl, or pyrazinyl;
wherein $R^5$ and $R^6$ are independently from another selected from hydrogen, $C_{1-4}$alkyl, polyhalo$C_{1-4}$alkyl, aminosulfonyl, or $C_{1-8}$alkylsulfonyl; or $R^7$-carbonyl;
wherein $R^5$ and $R^6$ are taken together with the nitrogen atom bearing $R^5$ and $R^6$ may form a pyrrolidinyl, piperidinyl, piperazinyl or morpholinyl ring; and
wherein $R^7$ is $C_{1-4}$alkyl, hydroxy, amino, mono- or di-($C_{1-4}$alkyl)amino, (hydroxy$C_{1-4}$alkyl)amino, ($C_{1-4}$alkyloxy$C_{1-4}$alkyl)amino, di($C_{1-4}$alkyl)amino$C_{1-4}$alkyl, pyrrolidinyl, piperidinyl, morpholinyl, or N-methylpiperazinyl;
or a pharmaceutically acceptable acid addition salt thereof, or a solvate thereof.

As used in the foregoing definitions:
 halo is generic to fluoro, chloro, bromo and iodo;
 $C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like;
 $C_{1-6}$alkyl is meant to include $C_{1-4}$alkyl and the higher homologues thereof having 5 or 6 carbon atoms, such as, for example, 2-methylbutyl, pentyl, hexyl and the like;
 $C_{1-8}$alkyl is meant to include $C_{1-6}$alkyl and the higher homologues thereof having 7 to 8 carbon atoms, such as for instance heptyl, ethylhexyl, octyl, and the like;
 polyhalo$C_{1-4}$alkyl is defined as polyhalosubstituted $C_{1-4}$alkyl, in particular $C_{1-4}$alkyl (as hereinabove defined) substituted with 2 to 6 halogen atoms such as difluoromethyl, trifluoromethyl, trifluoroethyl, and the like;

$C_{3-6}$cycloalkyl is generic to cyclopropyl, cyclobutyl, cyclopentyl, and cyclohexyl;

$C_{3-8}$cycloalkyl is generic to cyclopropyl, cyclobutyl, cyclopentyl, cyclohexyl, cycloheptyl and cyclooctyl;

$C_{6-8}$cycloalkyl is generic to cyclohexyl, cycloheptyl and cyclooctyl.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration.

Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art while using well-known methods such as, for example, X-ray diffraction.

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

Interesting compounds of formula (I) are those compounds of formula (I) wherein one or more of the following restrictions apply:

a) n is an integer 0, or n is an integer 2; or
b) X is $SO_2$; or
c) X is N—(CO)—$R^1$ wherein $R^1$ is hydrogen; or
d) X is N—(CO)—$R^1$ wherein $R^1$ is $C_{1-6}$alkyl, preferably methyl or ethyl; or
e) X is N—(CO)—$R^1$ wherein $R^1$ is $C_{1-6}$alkyloxy, preferably methyloxy; or
f) X is N—(CO)—$R^1$ wherein $R^1$ is $C_{1-4}$alkyloxy$C_{1-4}$alkyl, preferably methyloxymethyl; or
g) X is N—(CO)—$R^1$ wherein $R^1$ is polyhalo$C_{1-6}$alkyl, preferably trifluoromethyl; or
h) $R^2$ is $C_{1-6}$alkyl, in particular $R^2$ is tert-butyl or —$CH_2$-tert-butyl; or
i) $R^3$ is hydrogen; or
j) $R^4$ is $C_{1-8}$alkyl, $C_{1-8}$alkyl substituted with $C_{3-8}$cycloalkyl, polyhalo$C_{1-8}$alkyl; or
k) $R^4$ is $C_{1-8}$alkyl substituted with hydroxy, $C_{1-4}$alkyloxy, cyano; or
l) $R^4$ is aryl; or
m) $R^4$ is heteroaryl.

In an embodiment, the present invention relates to those compounds of formula (I) including any stereochemically isomeric forms thereof, wherein n is an integer 0, 1 or 2; X is $SO_2$ or N—(CO)—$R^1$; $R^1$ is hydrogen, $C_{1-6}$alkyl, $C_{1-6}$alkyloxy, $C_{1-4}$alkyloxy-$C_{1-4}$alkyl; or polyhalo$C_{1-6}$alkyl; $R^2$ is $C_{1-6}$alkyl; $R^3$ is hydrogen; $R^4$ is $C_{1-8}$alkyl; $C_{1-8}$alkyl substituted with $C_{3-8}$cycloalkyl; polyhalo$C_{1-8}$alkyl; $C_{3-8}$cycloalkyl; $C_{1-8}$alkyl substituted with hydroxy, $C_{1-4}$alkyloxy, cyano, or aryl; aryl; or heteroaryl; wherein aryl is phenyl substituted with halo $C_{1-4}$alkyloxy or cyano; and heteroaryl is thiazolyl or pyridinyl; or the pharmaceutically acceptable acid addition salts thereof, or the solvates thereof.

Compounds of formula (I-a), defined as compounds of formula (I) wherein n is 0, can be prepared by reacting intermediate (II) with an intermediate (III), wherein L is a leaving group such as halo, methanesulfonyloxy, benzenesulfonyloxy, trifluoro-methanesulfonyloxy and the like reactive leaving groups, in the presence of a suitable base such as $Cs_2CO_3$ in a reaction-inert solvent such as e.g. 2-propanone, 1,4-dioxane or THF. Depending upon the type of substituents present in intermediate (III) it may be necessary to introduce protecting groups in intermediate (III) which can be removed after the coupling reaction.

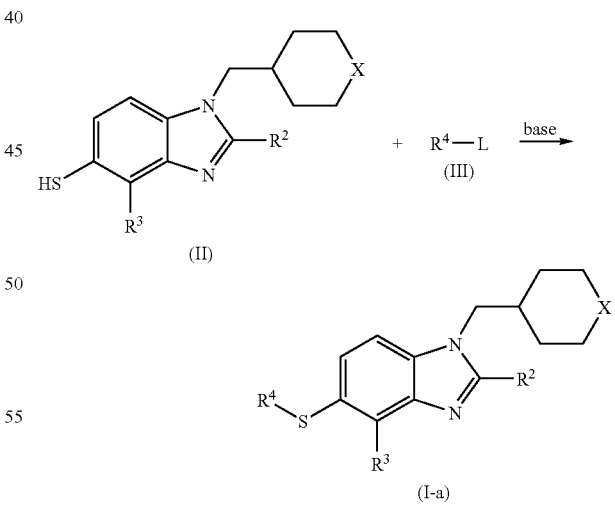

Compounds of formula (I-a), defined as compounds of formula (I) wherein n is 0, can also be prepared by reacting intermediate (II) with an intermediate (IV) in the presence of a suitable base such as $Cs_2CO_3$, a catalyst such as $Pd_2(dba)_3$ and a suitable ligand such as Xantphos, in a reaction-inert solvent such as e.g. 2-propanone, 1,4-dioxane or THF while heating under conventional or microwave conditions.

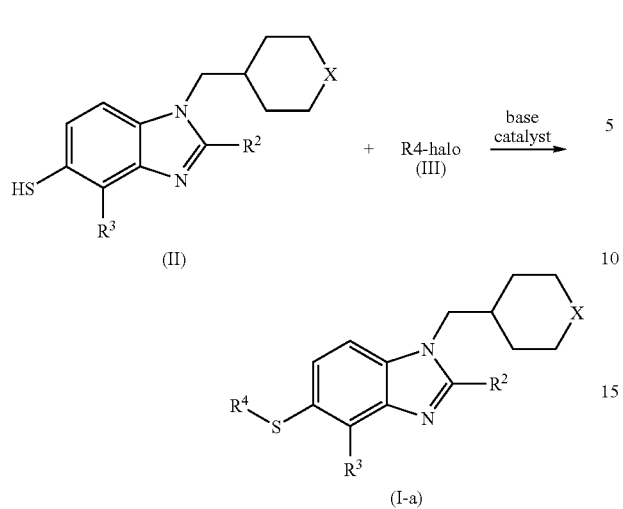

zenesulfonyloxy, trifluoromethanesulfonyloxy and the like reactive leaving groups. The reaction can be performed in a reaction-inert solvent such as, for example, acetonitrile or dichloromethane, and optionally in the presence of a suitable base such as, for example, sodium carbonate, potassium carbonate or triethylamine. Stirring may enhance the rate of the reaction. The reaction may conveniently be carried out at a temperature ranging between room temperature and the reflux temperature of the reaction mixture.

Compounds of formula (I-a) can be converted into compounds of formula (I-b), defined as compounds of formula (I) wherein n represents 1, or into compounds of formula (I-c), defined as compounds of formula (I) wherein n represents 2, by art known S-oxidation reactions.

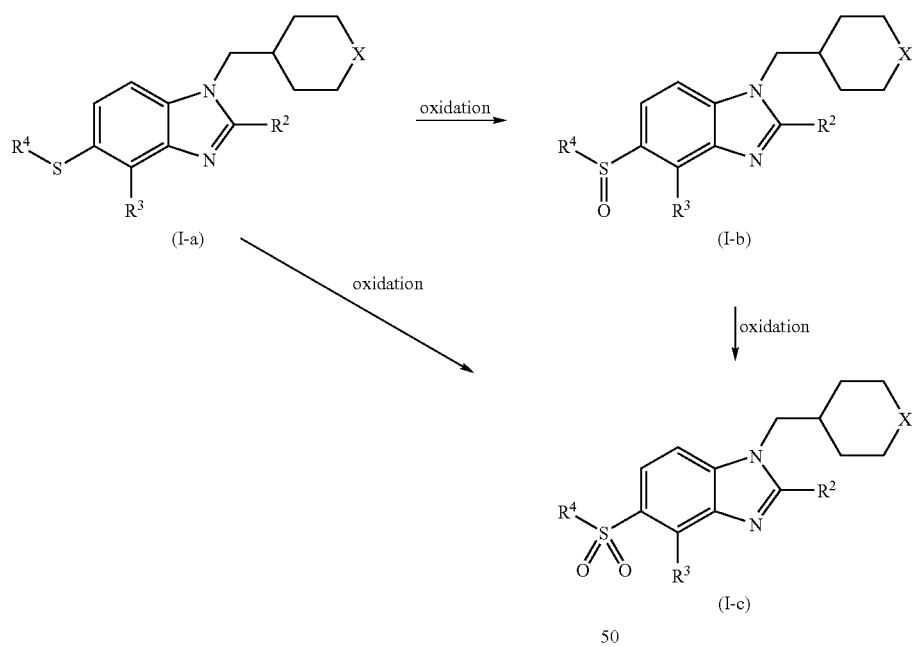

S-oxidation reactions can be performed using a 30% aqueous solution of hydrogen peroxide, or by other oxidizing agents such as, $NaIO_4$, tert-butyloxychloride, acyl nitrites, sodium perborate and peracids such as mCPBA (meta-chloroperbenzoic acid). Sulfides can be oxidized to sulfoxides which can be further oxidized to sulfones by addition of another equivalent of hydrogen peroxide, $KMnO_4$, sodium perborate, potassium hydrogen persulfate, mCPBA or the like reagents. If enough oxidizing agent is present, sulfides can be converted directly to sulfones without isolation of the sulfoxides.

Compounds of formula (I-d), defined as compounds of formula (I) wherein X represents N—(CO)—$R^1$, by N-alkylating an intermediate (V) with an intermediate (VI), wherein W is an appropriate leaving group such as, for example, halo, e.g. fluoro, chloro, bromo, iodo, or in some instances W may also be a sulfonyloxy group, e.g. methanesulfonyloxy, ben- -continued

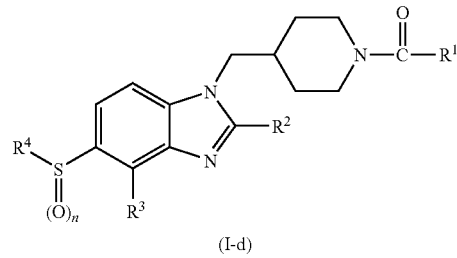

Compounds of formula (I-e), defined as compounds of formula (I) wherein n is 2 and R1 is defined as other than hydrogen, can be prepared as described in Scheme 1.

Scheme 1

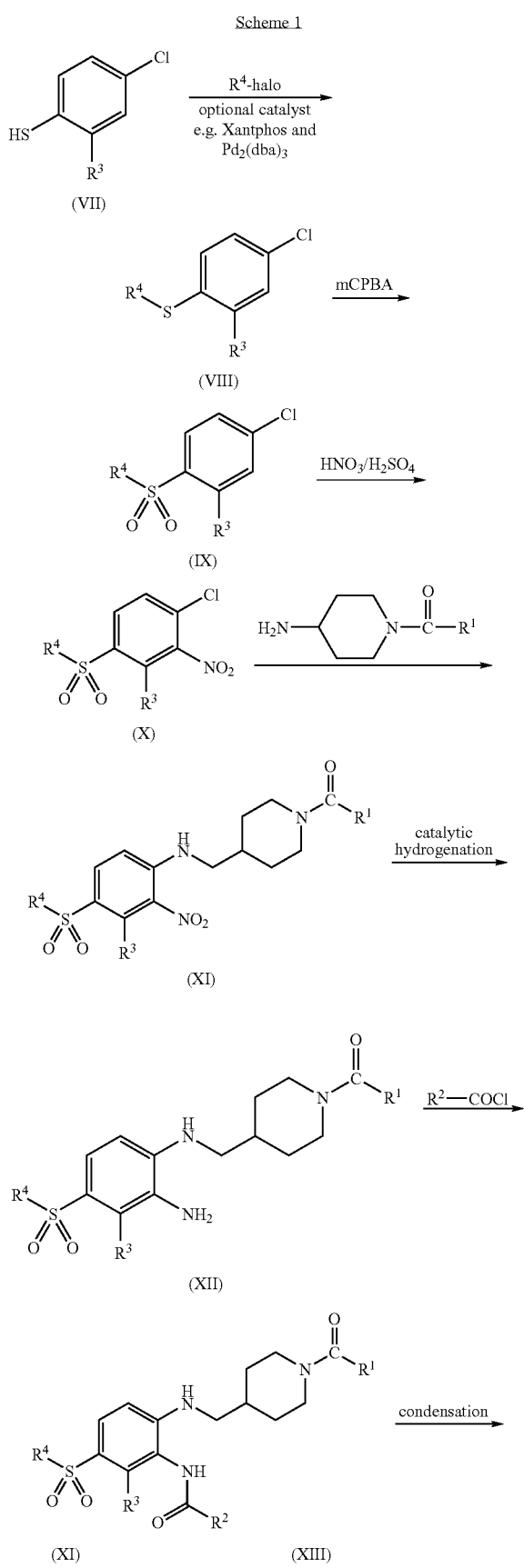

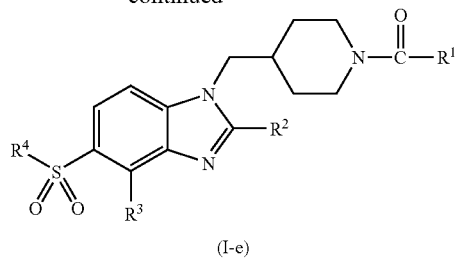

The condensation reaction for obtaining compounds of formula (I-e) can be performed under acidic or basic conditions. Under acidic conditions, the condensation is done in the presence of an organic acid such as acetic acid, or an inorganic acid such as HCl or $H_2SO_4$, or a combination thereof, in a solvent such as acetic acid, $H_2O$, methanol, ethanol, dioxane, toluene, or dichloroethane. Under basic conditions, the condensation reaction is performed in the presence of an inorganic base such as e.g. $K_2CO_3$ in a reaction-inert solvent such as DMSO, or in an alcoholic NaOH solution The reaction may conveniently be carried out at a temperature ranging between room temperature and the reflux temperature of the reaction mixture. Reaction rate and yield may be enhanced by microwave assisted heating e.g. at 190° C. in dichloroethane as solvent, possibly eliminating the need of an additionally added acid or base.

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereo specifically. Preferably if a specific stereoisomer is desired, said compound will be synthesized by stereospecific methods of preparation. These methods will advantageously employ enantiomerically pure starting materials.

The compounds of formula (I), the pharmaceutically acceptable salts and stereoisomeric forms thereof possess selective cannabinoid recepter 2 (CB2) agonistic properties as demonstrated in the Pharmacological Examples. Pharmacological example C.1 describes the methodology to measure CB2 agonism and results are listed in Table C.1.

Therefore the present compounds of formula (I) are useful as a medicine especially in the treatment of a condition or disease mediated by the cannabinoid 2 receptor, in particular CB2 agonistic activity. Subsequently the present compounds may be used for the manufacture of a medicine for treatment of a condition or a disease mediated by CB2 receptor activity, in particular CB2 agonistic activity.

Preferably, the present invention also provides the use of a compound of formula (I) or a pharmaceutically acceptable salt thereof for the manufacture of a medicament for the treatment of conditions or diseases selected from CB2 conditions or diseases.

Further, the present invention provides a method of treatment of a condition mediated by CB2 receptor activity, in a mammalian subject, which comprises administering to a mammal in need of such treatment a therapeutically effective amount of a compound of formula (I) or a pharmaceutically acceptable salt thereof.

Cannabinoid receptor 2 mediated conditions or disorders are e.g. cardiovascular diseases, such as e.g. atherosclerosis, hypertension, myocardial ischemia; chronic pain disorders, such as e.g. hyperalgesia, neuropathic pain, peripheral pain, visceral pain, inflammatory pain, thermal hyperalgesia, nociceptive pain, fibromyalgia, chronic low back pain, and dental pain; inflammation, oedema, bladder inflammation, neuroinflammatory diseases, immune system disorders, autoimmune diseases, multiple sclerosis, rheumatoid arthritis, gastrointestinal disorders, intestinal motility disorders, irritable bowel syndrome (IBS), inflammatory bowel disease (IBD), Crohn's disease, chronic liver injury (cirrhosis), cancer, prostate cancer, cancer pain, glioma, allergy, nausea and vomiting, asthma, chronic obstructive pulmonary diseases, psoriasis, epilepsy, and bone loss disorders, such as e.g., osteoporosis (hereinafter, referred as 'CB2 disorders or diseases').

The term "treating" and 'treatment', as used herein, refers to curative, palliative and prophylactic treatment, including reversing, alleviating, inhibiting the progress of, or preventing the disease, disorder or condition to which such term applies, or one or more symptoms of such disease, disorder or condition.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intramuscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, c.g. sterile pyrogen-free water, before use.

The compounds of formula (I) may also be formulated in rectal compositions such as suppositories or retention enemas, e.g. containing conventional suppository bases such as cocoa butter and/or other glycerides.

Those of skill in the treatment of diseases linked to the mediation of the cannabinoid receptors will easily determine the therapeutically effective amount of a compound of formula (I) from the test results presented hereinafter. In general it is contemplated that a therapeutically effective dose will be from about 0.001 mg/kg to about 50 mg/kg of body weight, more preferably from about 0.01 mg/kg to about 10 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

As used herein, a "therapeutically effective amount" of a compound, is the quantity of a compound which, when administered to an individual or animal, results in a sufficiently high level of that compound in the individual or animal to cause a discernible increase or decrease in stimulation of cannabinoid receptors.

The exact dosage and frequency of administration depends on the particular compound of formula (I) used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines.

EXPERIMENTAL PART

In the procedures described hereinafter the following abbreviations were used: 'DCM' stands for dichloromethane, 'MeOH' stands for methanol, 'NH$_3$' stands for ammonia, 'CH$_3$CN' stands for acetonitrile, 'THF' stands for tetrahydrofuran, 'DIPE' stands for diisopropylether, 'NaBH$_3$(CN)' stands for sodium cyanotrihydroborate, 'Cs$_2$CO$_3$' means cesium carbonate, 'MgSO$_4$' means magnesium sulphate, 'NaHCO$_3$' means carbonic acid monosodium salt, 'NaOH' means sodium hydroxide, 'Pd$_2$(dba)$_3$' means tris[μ-[(1,2-η:4,5-η)-(1E,4E)-1,5-diphenyl-1,4-pentadien-3-one]]dipalladium and 'Xantphos' means (9,9-dimethyl-9H-xanthene-4,5-diyl)bis[diphenylphosphine], 'DMSO' means dimethylsulfoxide; 'DMAP' means 4-(dimethylamino)pyridine, 'HBTU' means 1-[bis(dimethylamino)methylene]-1H-benzotriazoliumhexafluoro-phosphate(1-)3-oxide.

Isolute HM-N™ filter is a product of Argonaut, Foster City, Calif. 94404, USA, and is a short column comprising a modified form of diatomaceous earth that can remove water from a sample in combinatorial chemistry applications.

High-Performance Liquid Chromatography Purification Methods:

Purification Method A

The product was purified by reversed-phase high-performance liquid chromatography (Shandon Hyperprep® C18 BDS (Base Deactivated Silica) 8 μm, 250 g, I.D. 5 cm). Two mobile phases were used (phase A: a 0.25% NH$_4$HCO$_3$ solution in water; phase B: CH$_3$CN). First, 85% A and 15% B with a flow rate of 40 ml/min was hold for 0.5 minutes. Then a gradient was applied to 10% A and 90% B in 41 minutes with a flow rate of 80 ml/min. Then a gradient was applied to 100% C in 20 minutes with a flow rate of 80 ml/min and hold for 4 minutes.

Purification Method B

The product was purified by reversed phase high-performance liquid chromatography (Shandon Hyperprep® C18 BDS (Base Deactivated Silica) 8 μm, 250 g, I.D. 5 cm). A gradient with three mobile phases was applied (phase A: a 0.25% NH$_4$HCO$_3$ solution in water; phase B: CH$_3$OH; phase C: CH$_3$CN). The desired fractions were collected and worked-up.

A. Synthesis of the Intermediates

Example A.1 a) Preparation of

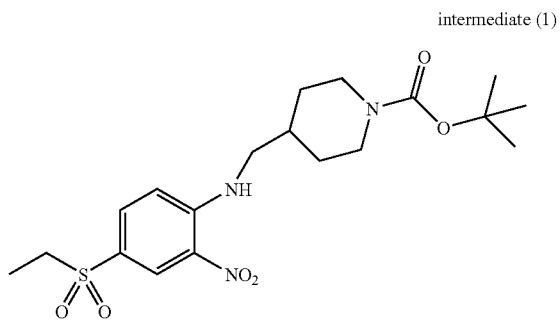

intermediate (1)

Potassium carbonate (4.55 g, 0.033 mol) was added to a mixture of 1-chloro-4-(ethylsulfonyl)-2-nitrobenzene (7.5 g, 0.03 mol) and 4-aminomethyl-piperidine-1-carboxylic acid tert-butyl ester (7.72 g, 0.036 mol) in dioxane (120 ml). The reaction mixture was stirred for 3 hours at 75-80° C. and then for 3 hours at 100° C. The solids were filtered off and the reaction mixture was evaporated. The residue was dissolved in DCM (200 ml). The organic layer was washed with water (200 ml). The water layer was extracted with DCM (150 ml). The combined organic layers were dried (MgSO$_4$), filtered and the solvent was evaporated, yielding 12.1 g of intermediate (1).

b) Preparation of

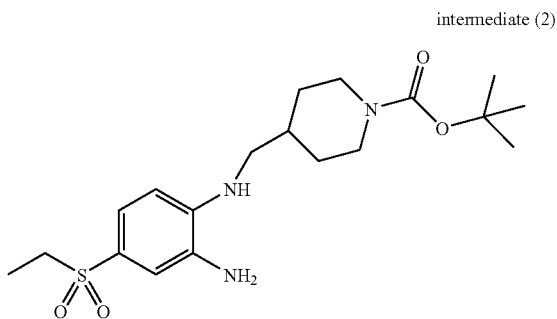
intermediate (2)

A mixture of intermediate (1) (12.1 g) in methanol (150 ml) was hydrogenated with palladium on activated carbon (10%) (2 g) as a catalyst in the presence of a thiophene solution (1 ml) and vanadium oxide (0.2 g). After uptake of hydrogen (3 equivalents), the reaction mixture was filtered over dicalite and the filtrate was evaporated, yielding intermediate (2).

c) Preparation of

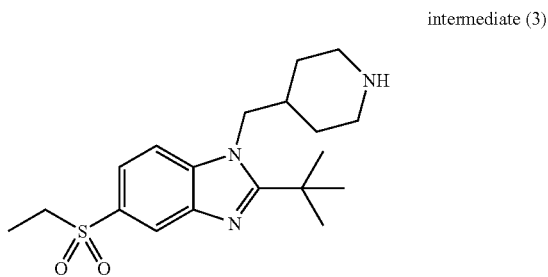
intermediate (3)

A mixture of intermediate (2) (0.014 mol), 2,2-dimethylpropanoyl chloride (2.1 ml, 0.017 mol) and pyridine (2 ml) in DCM (90 ml) was stirred overnight at room temperature. The solvent was evaporated and acetic acid (80 ml) and hydrochloric acid (8 ml) were added to the residue. This mixture was refluxed for 3 hours and then the mixture was evaporated. The residue was partitioned between DCM (300 ml) and water (250 ml). The mixture was basified with aqueous $NH_3$ and the layers were separated. The separated organic layer was washed with water, dried ($MgSO_4$), filtered and the solvent was evaporated, yielding 3.4 g of residue. This residue was purified by column chromatography over silica gel (Biotage; eluent: DCM/(MeOH/$NH_3$) from 99/1 till 92/8. The desired fractions were collected and the solvent was evaporated, yielding 2.7 g of intermediate (3).

Example A.2 a) Preparation of

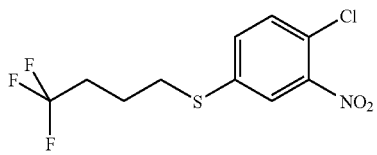
intermediate (4)

A mixture of 4-chlorobenzenethiol (0.2 mol) and 1,1,1-trifluoro-4-iodobutane (0.21 mol) in 2-propanone (1000 ml) was cooled on an ice-bath. $Cs_2CO_3$ (0.215 mol) was added and the reaction mixture was stirred overnight under nitrogen flow at room temperature. Then, DIPE (1000 ml) was added, the solid was filtered off and the filtrate was evaporated, yielding intermediate (4).

b) Preparation of

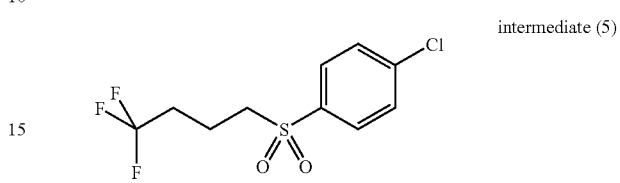
intermediate (5)

A mixture of intermediate (4) (0.2 mol) in trichloromethane (1200 ml) was cooled on an ice-bath. 3-Chlorobenzenecarboperoxoic acid (100 g; 70-75%) was added portionwise over 20 minutes and the reaction mixture was stirred for 210 minutes at room temperature. The mixture was cooled on an ice-bath and an aqueous NaOH solution (1000 ml, 5%) was added. The separated organic layer was washed twice with the aqueous NaOH solution (1000 ml, 5%) and then washed with water. The combined organic layers were dried ($MgSO_4$), filtered and the solvent was evaporated, yielding 57 g of intermediate (5).

c) Preparation of

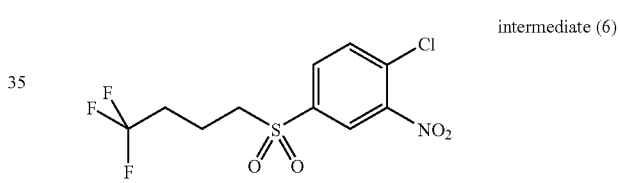
intermediate (6)

A mixture of concentrated sulfuric acid and nitric acid (50/50) (100 ml) was added dropwise over 1 hour to a mixture of intermediate (5) (0.2 mol) in concentrated sulfuric acid (500 ml), while the reaction mixture was cooled with cold water. The mixture was stirred for 2 hours at room temperature and was then poured on ice (2000 ml). The precipitate was filtered off, washed with water and dried (vacuum), yielding 66 g of intermediate (6).

d) Preparation of

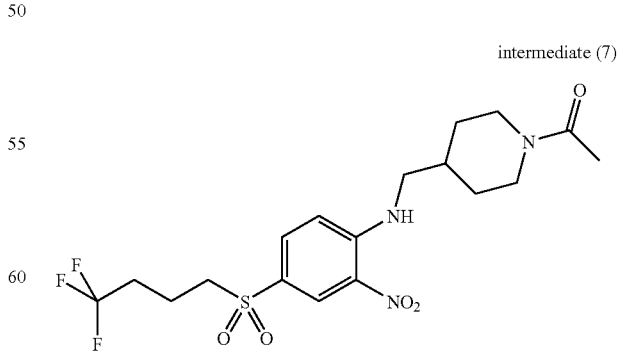
intermediate (7)

A mixture of intermediate (6) (0.002 mol), 1-acetyl-4-piperidinemethanamine (0.00235 mol) and triethylamine (0.003 mol) in DMSO (4 ml) was stirred overnight at 100° C.

This mixture was poured on ice-water and extracted with DCM. The organic layer was washed twice with water, dried (MgSO₄) and the solvent was evaporated. The residue was purified by combiflash column chromatography over silica gel (eluent: DCM/(CH₃OH/NH₃) from 100/0 to 97/3). The product fractions were collected and the solvent was evaporated, yielding 0.4 g of intermediate (7).

e) Preparation of intermediate (8)

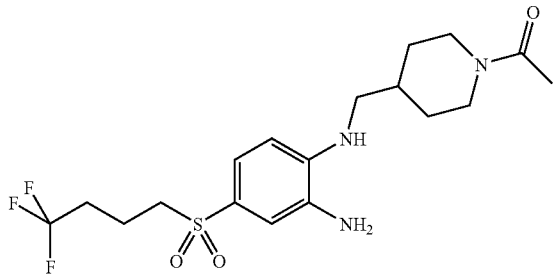

A mixture of intermediate (7) (0.0009 mol) in methanol (40 ml) was hydrogenated with palladium on activated carbon (10%) (0.1 g) as a catalyst in the presence of a thiophene solution (0.1 ml). After uptake of hydrogen (3 equivalents), the catalyst was filtered off over celite and the filtrate was evaporated, yielding intermediate (8) (used as such in the next step).

Example A.3 a) Preparation of intermediate (10)

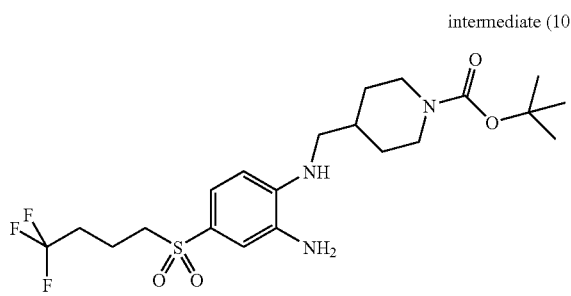

A mixture of intermediate (6) (0.008 mol), 4-aminomethyl-piperidine-1-carboxylic acid tert-butyl ester (0.0093 mol) and triethylamine (0.012 mol) in DMSO (15 ml) was stirred overnight in a closed vessel at 100° C. The reaction mixture was cooled to 60° C. and then poured on ice-water (200 ml). The yellow mixture was stirred for 30 minutes at room temperature, the yellow precipitate was filtered off, washed with large amounts of water and dried (vacuum), yielding 3.95 g of intermediate (10).

b) Preparation of intermediate (11)

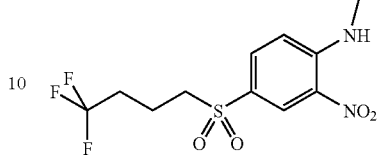

A mixture of intermediate (10) (0.00738 mol) in methanol (100 ml) was hydrogenated with palladium on activated carbon (10%) (1 g) as a catalyst in the presence of a thiophene solution (0.5 ml). After uptake of hydrogen (3 equivalents), the catalyst was filtered off over celite and the filtrate was evaporated, yielding intermediate (11).

c) Preparation of intermediate (12)

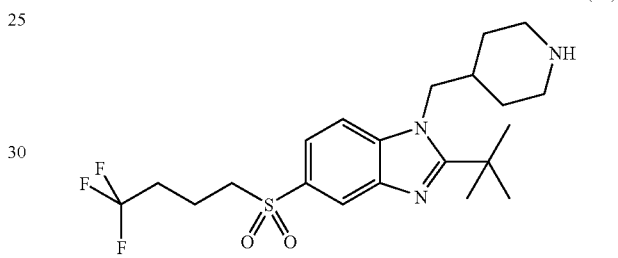

A mixture of intermediate (11) (max. 0.00768 mol; crude), 2,2-dimethylpropanoyl chloride (0.0096 mol) and pyridine (2 ml) in DCM (50 ml) was stirred at room temperature for 2 hours. The solvent was evaporated and acetic acid (50 ml) and hydrochloric acid (concentrated) (5 ml) were added to the residue. This mixture was stirred for 3 hours at 120° C. The mixture was cooled and the solvent was evaporated. The residue was partitioned between DCM and an aqueous NH₃ solution. The separated organic layer was washed with brine, dried (MgSO₄) and the solvent was evaporated. The crude residue was purified by combiflash column chromatography over silica gel (eluent: DCM/(CH₃OH/NH₃) 92/8). The product fractions were collected and the solvent was evaporated, yielding 2.65 g of intermediate (12).

Example A.4 a) Preparation of intermediate (13)

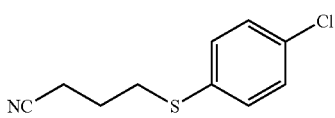

A mixture of 4-chlorobenzenethiol (0.1 mol) and 4-bromobutanenitrile (0.15 mol) in acetone (500 ml) was stirred. Cs₂CO₃ (0.11 mol) was added and the reaction mixture was stirred under nitrogen. DIPE (500 ml) was added and the precipitate was filtered off. The filtrate was evaporated, yielding intermediate (13).

b) Preparation of

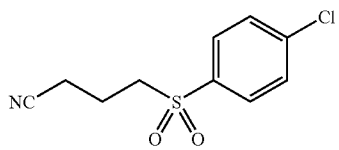 intermediate (14)

A mixture of intermediate (13) (0.1 mol) in trichloromethane (500 ml) was cooled on ice while 3-chlorobenzenecarboperoxoic acid (0.22 mol) was added portion-wise. The reaction mixture was stirred at room temperature for 3 hours. The organic layer was washed with a NaOH-solution (500 ml, 1N NaOH, 3×) and with water. The organic layer was dried (MgSO$_4$), filtered and the solvent was evaporated, yielding 35 g of intermediate (14).

c) Preparation of

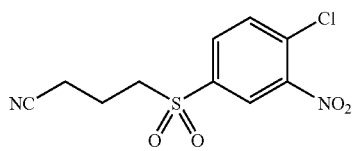 intermediate (15)

Sulfuric acid (120 ml) was cooled on a salt/icebath (−10° C.). Intermediate (14) (0.05 mol) was added to the mixture, followed by the dropwise addition of a mixture of sulphuric acid and nitric acid (1:1) (20 ml) over 30 minutes. The mixture was heated to room temperature and became a yellow, orange solution. After stirring for 1 hour at room temperature, the reaction mixture was poured on ice-water and the light yellow solid was filtered off and washed with water. The precipitate was dried (vacuum), yielding 13.5 g of residue. The residue was triturated at room temperature with DCM and the remaining solid was filtered off. The filtrate was evaporated and dried, yielding 7.1 g of intermediate (15).

d) Preparation of

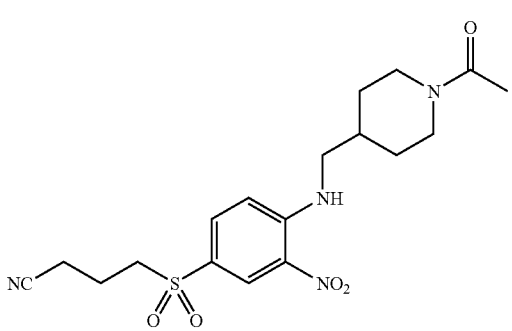 intermediate (16)

A mixture of intermediate (15) (0.002 mol), 1-acetyl-4-piperidinemethanamine (0.00235 mol) and triethylamine (ca. 0.003 mol) in DMSO (5 ml) was stirred overnight at 100° C. The mixture was poured on icewater and extracted with DCM. The organic layer was washed twice with water, dried (MgSO$_4$) and the solvent was evaporated. The residue was purified by column chromatography over silica gel (eluent: DCM/(CH$_3$OH/NH$_3$) from 100/0 to 96/4). The product fractions were collected and the solvent was evaporated, yielding 0.41 g of intermediate (16).

e) Preparation of

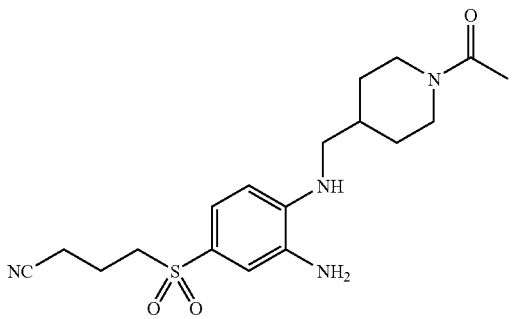 intermediate (17)

A mixture of intermediate (16) (ca. 0.001 mol) in methanol (40 ml) was hydrogenated with palladium on activated carbon (10%) (0.1 g) as a catalyst in the presence of a thiophene solution (0.1 ml). After uptake of hydrogen (3 equivalents), the catalyst was filtered off over celite and the filtrate was evaporated. The residue was used as such in the next step, yielding intermediate (17).

Example A.5 a) Preparation of

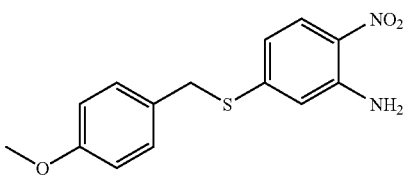 intermediate (18)

A mixture of 5-chloro-2-nitrobenzenamine (0.16 mol), 4-methoxybenzenemethanethiol (0.16 mol) and potassium hydroxide (0.30 mol) in ethanol (500 ml) was stirred and refluxed for 2 hours. The reaction mixture was cooled. The precipitate was filtered off, washed with ethanol and dried, yielding 48.5 g of intermediate (18).

b) Preparation of

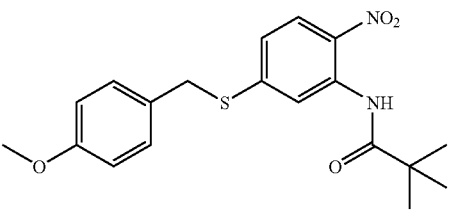 intermediate (19)

A solution of 2,2-dimethylpropanoyl chloride (0.032 mol) in DCM (20 ml) was added dropwise to a mixture of intermediate (18) (0.03 mol) and pyridine (0.06 mol) in DCM (180 ml), cooled on an ice bath. The reaction mixture was allowed to reach room temperature. DMAP was added and the mixture was stirred and refluxed for 20 hours. Extra intermediate (18) (0.01 mol), 2,2-dimethylpropanoyl chloride (0.048 mol) and pyridine (1.2 mol) were added. The mixture was refluxed for 2 hours. The solvent was evaporated. The residue was taken up into DCM and washed with water. The organic layer was separated, dried (MgSO₄), filtered and the solvent was evaporated. The residue was crystallized from DIPE. The precipitate was filtered off, washed and dried, yielding 9.1 g of intermediate (19).

c) Preparation of

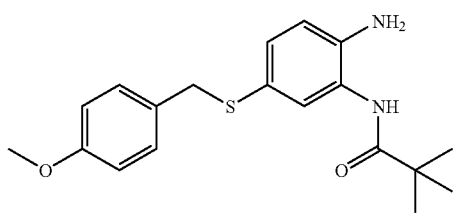

intermediate (20)

A mixture of intermediate (19) (0.0748 mol), iron (56 g) and acetic acid (10 ml) in water (500 ml) was stirred and refluxed for 4 hours. The mixture was cooled. The solvent was decanted. The residue was taken up into methanol and THF. The mixture was filtered over dicalite. The solvent was evaporated. The residue was taken up into DCM. The organic layer was separated and filtered over MgSO₄ and dicalite. The solvent was evaporated. The residue was crystallized from DIPE. The precipitate was filtered off and dried, yielding 21 g of intermediate (20).

d) Preparation of

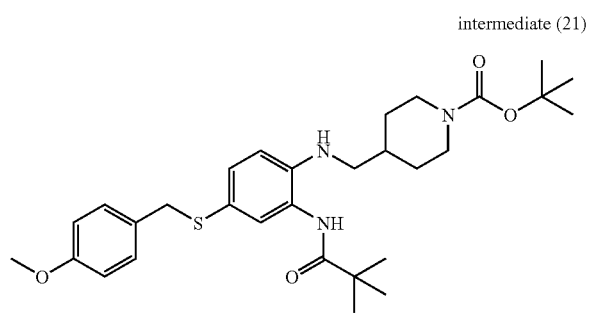

intermediate (21)

To intermediate (20) in DCM (250 ml) was added 4-formyl-1-piperidinecarboxylic acid tert-butyl ester, then acetic acid and titanium (IV) isopropoxide. The reaction mixture was stirred for 20 minutes. Then NaBH₃(CN) was added, the reaction mixture was stirred for 2 hours. Water was added to the reaction mixture, the organic layer was separated, dried (MgSO₄), filtered and evaporated, yielding 20 g of intermediate (21).

e) Preparation of

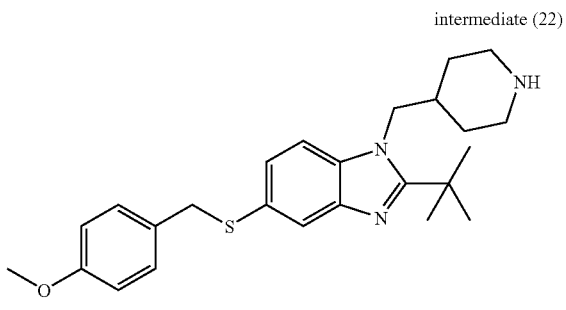

intermediate (22)

Intermediate (21), acetic acid and hydrochloric acid (concentrated) were stirred at reflux temperature overnight. The reaction mixture was concentrated. The residue taken up in water (500 ml), basified with NaHCO₃, and extracted with three times with 300 ml DCM. The combined organic layer was washed with brine, dried on MgSO₄ and concentrated to give 11.4 g of intermediate (22).

Example A.6

Preparation of

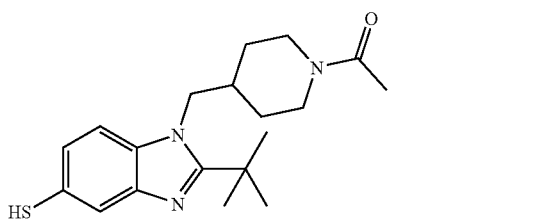

intermediate (23)

Compound (11) and trifluoroacetic acid were stirred at 120° C. for 60 minutes in a microwave. The reaction mixture was cooled. The solvent was evaporated. The residue was taken up in ethyl acetate and then washed with H₂O/NaHCO₃ solution. The organic layer was dried (MgSO₄), filtered and evaporated yielding 2.3 g of intermediate (23).

The following intermediate was prepared analogously from compound (44):

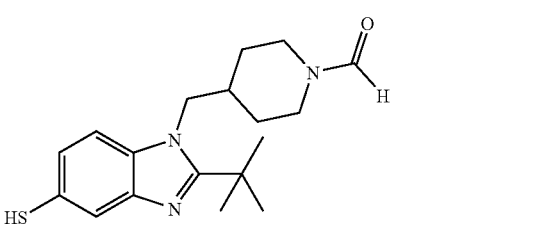

intermediate (24)

Example A.7 a) Preparation of

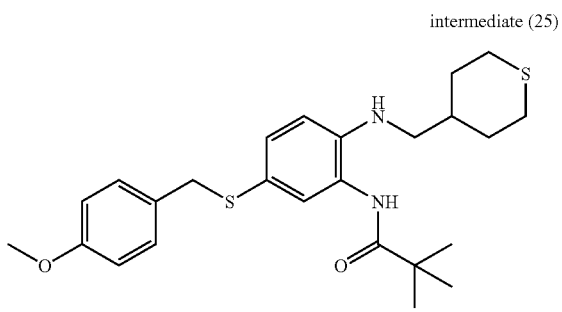
intermediate (25)

Reaction under nitrogen flow. Methyl tetrahydro-2H-thiopyran-4-yl-ketone (0.039 mol; 50% solution in ethanol) was added to a mixture at room temperature of intermediate (20) (0.03 mol) in DCM (32 ml) and acetic acid (4 ml) and then stirred for 5 minutes. NaBH$_3$(CN) (0.04 mol) was added to the reaction mixture and then stirred for 1 hour at room temperature. The reaction mixture was washed with water. The separated organic layer was dried (MgSO$_4$), filtered and the solvent was evaporated. The residue was suspended in DIPE. The precipitate was filtered off and dried (vacuum, room temperature), yielding 11.2 g of intermediate (25).

b) Preparation of

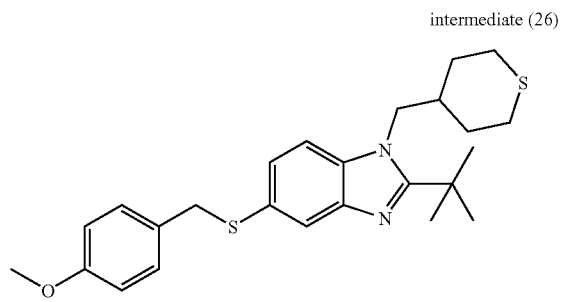
intermediate (26)

A mixture of intermediate (25) and acetic acid was heated for 100 minutes at 150° C. in a microwave. The solvent was evaporated. The residue was taken up DCM and washed with water/NaHCO$_3$. The organic layer was dried (MgSO$_4$), filtered and evaporated. The residue was purified over a short filter with silicagel and DCM MeOH/NH$_3$ (from 100 to 97:3) as eluent. The product fractions were collected and evaporated, yielding 1.3 g of intermediate (26).

c) Preparation of

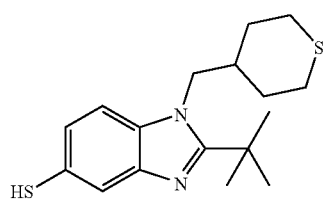
intermediate (27)

Intermediate (26) and trifluoroacetic acid were stirred at 120° C. for 30 minutes in a microwave. The reaction mixture was cooled. The solvent was evaporated. The residue was taken up in ethyl acetate and then washed with water/NaHCO$_3$ solution. The organic layer was dried (MgSO$_4$), filtered and evaporated. The crude residue was used in the next step, yielding 1.3 g of intermediate (27).

Example A.9

Preparation of

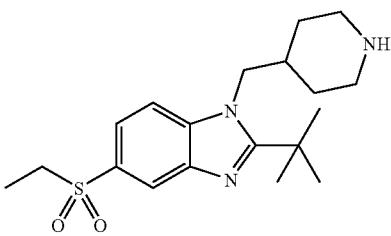
intermediate (28)

A mixture of intermediate (2) (0.0047 mol), tert-butylacetyl chloride (0.81 g, 0.006 mol) and pyridine (2 ml) in DCM (20 ml) was stirred overnight at room temperature. The solvent was evaporated. Acetic acid (25 ml) and HCl (2 ml) were added to the residue. This mixture was stirred at 190° C. in the microwave oven for 75 minutes (in 2 portions). The solvent was evaporated. The residue was partitioned between DCM (250 ml) and an aqueous NH$_3$ solution. The separated organic layer was washed with water, dried (MgSO$_4$), filtered and the solvent was evaporated, yielding a residue that was purified by column chromatography over silica gel (Biotage; eluent: CH$_2$Cl$_2$/(CH$_3$OH/NH$_3$) from 100/0 to 96, yielding 0.85 g of intermediate (28).

Example A. 10

Preparation of

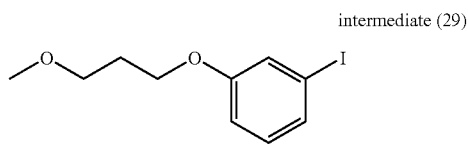
intermediate (29)

A mixture of 3-iodophenyl (10 mmol), 1-bromo-3-methoxypropane (14.7 mmol) and K$_2$CO$_3$ (20.26 mmol) in acetone (10 ml) was stirred at 50° C. for 40 hours. The salts were filtered off and washed. The filtrate was concentrated and the residue was purified by column chromatography using ethyl acetate/heptane (0:100 to 20:80) as eluent. The product fractions were collected and evaporated, yielding intermediate (29).

Example A.11

Preparation of

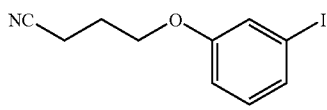

intermediate (30)

A mixture of 3-iodophenyl (10 mmol), 1-bromo-3-cyanopropane (14.7 mmol) and K₂CO₃ (20.26 mmol) in acetone (10 ml) was stirred at 50° C. for 40 hours. The salts were filtered off and washed. The filtrate was concentrated and the residue was purified by column chromatography using ethyl acetate/heptane (0:100 to 20:80) as eluent. The product fractions were collected and evaporated, yielding intermediate (30).

B. Synthesis of the Final Compounds

Example B.1

Preparation of

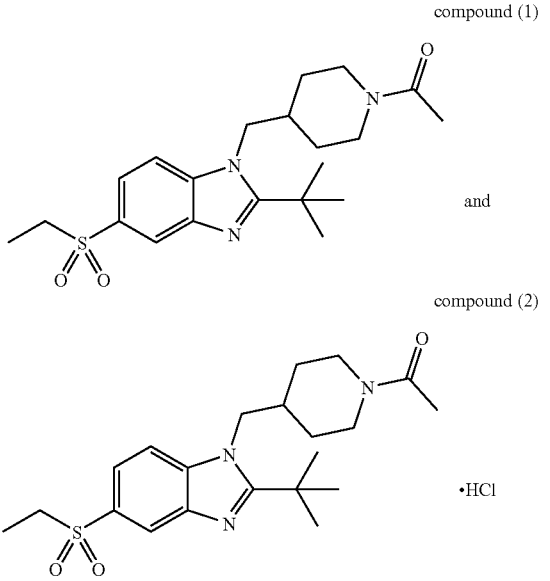

compound (1)

and compound (2)

A mixture of intermediate (3) (0.7 g, 0.00193 mol), acetyl acetate (0.26 g, 0.0025 mol) and DCM (20 ml) was reacted overnight at room temperature. The mixture was first washed with water (15 ml), then twice with an aqueous NH₃ solution (2×15 ml) and finally with brine (15 ml). The mixture was filtered over Isolute HM-N™ and then the solvent was evaporated under a stream of nitrogen. The residue was crystallized from DIPE, yielding 0.035 g of compound (1). The oily product was dissolved in 2-propanol (8 ml) and a HCl/2-propanol (6 N, 0.5 ml) solution was added. The solvent was evaporated. The residue was triturated with diethyl ether. The precipitate was filtered off and dried (vacuum), yielding 0.53 g of compound (2).

Compound (46) was prepared analogously by reacting intermediate (28) with acetic anhydride.

Example B.2

Preparation of

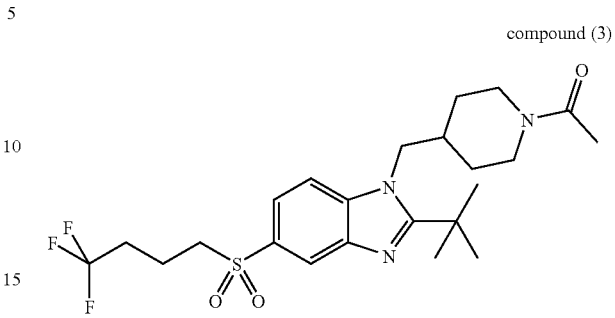

compound (3)

A mixture of intermediate (8) (max. 0.0009 mol), 2,2-dimethylpropanoyl chloride (0.170 ml) and pyridine (0.25 ml) in DCM (20 ml) was stirred at room temperature for 2 hours. The solvent was evaporated and 1,2-dichloroethane (4 ml) was added to the crude residue. The mixture was heated in the microwave for 1 hour at 190° C. The mixture was allowed to cool, and DCM (4 ml) and a NaOH solution (1 ml, 1N) were added. The reaction mixture was stirred, filtered over an Isolute HM-N™ filter and the solvent was evaporated. The product was purified by reversed-phase high-performance liquid chromatography. The product fractions were collected and the solvent was evaporated, yielding 0.123 g of compound (3).

Compound (10) was prepared analogously by reacting 2,2-dimethylpropanoyl chloride with intermediate (17) and compound (47) was prepared analogously by reacting intermediate (2) with 2,2-dimethylacetyl chloride.

Example B.3

Preparation of

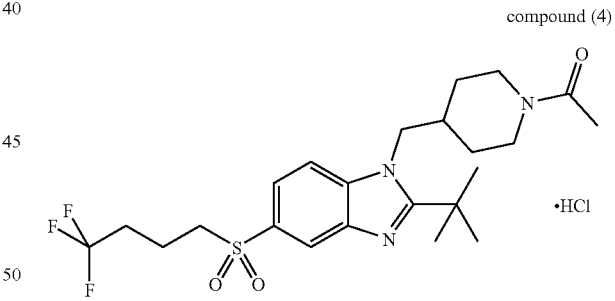

compound (4)

·HCl

A mixture of intermediate (12) (0.00061 mol), acetic acid anhydride (0.0008 mol) and triethyl amine (0.17 ml) in DCM (10 ml) was stirred overnight at room temperature. Water was added, the mixture was stirred and the layers were separated. The organic layer was dried by passing through an Isolute HM-N™ filter. The solvent was evaporated. The residue was crystallized in diethyl ether with hydrochloric acid, yielding 0.260 g of compound (4).

Compounds (6), (7), (8), and (9) were prepared analogously by reacting intermediate (12) respectively with propanoyl chloride, methoxycarbonyl chloride, bis(trifluoroacetic) anhydride or 2-methoxyacetyl chloride. Compound (11) was prepared analogously by reacting intermediate (22) with acetic anhydride in the presence of pyridine and THF as solvent.

Example B.4

Preparation of compound (5)

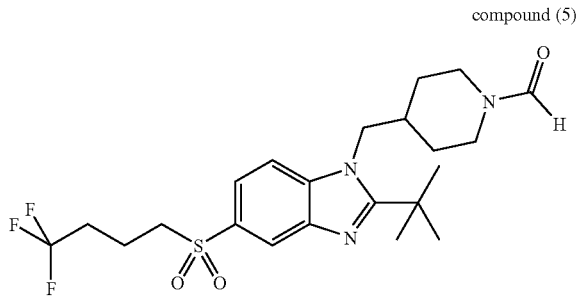

A mixture of intermediate (12) (0.000675 mol), formic acid (0.00087 mol), HBTU (0.00087 mol) and triethylamine (0.15 ml) in DCM (5 ml) was stirred at 50° C. After 2 hours, an extra portion of formic acid (0.00087 mol) was added and the mixture was stirred overnight at room temperature. Then DCM (5 ml) and water (1 ml) were added and the mixture was filtered over an Isolute HM-N™ filter. The solvent was evaporated and the residue was purified by reversed-phase high-performance liquid chromatography. The product fractions were collected and the solvent was evaporated, yielding 0.205 g of compound (5).

Example B.5

Preparation of compound (12)

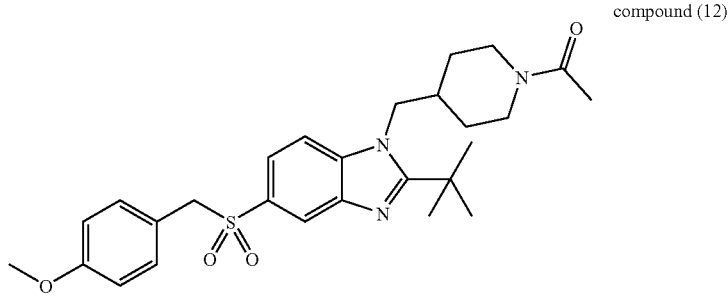

3-Chlorobenzenecarboperoxoic acid (0.0007 mol; 77%) was added to a mixture of compound (11) (0.0003 mol) in trichloromethane (10 ml) at room temperature. The reaction mixture was stirred for 30 minutes at room temperature and then water and NaOH (1N) was added. The separated organic layer was dried (MgSO$_4$), filtered and the solvent was evaporated. The residue was purified on a reversed phase column. The product fractions were collected and the solvent was evaporated and co-evaporated to dryness, yielding 0.075 g of compound (12).

Compound (49) was prepared analogously starting from intermediate (29). Compound (53) was prepared analogously starting from compound (50). Compounds (62) and (63) were prepared analogously starting from compound (54). Compound (73) was prepared analogously starting from compound (72). Compound (56) was prepared analogously starting from compound (52). Compound (61) was prepared analogously starting from compound (51). Compound (60) was prepared analogously starting from compound (57). Compound (59) was prepared analogously starting from compound (58). Compound (67) was prepared analogously starting from compound (65). Compound (68) was prepared analogously starting from compound (66). Compound (64) was prepared analogously starting from compound (74). Compound (69) was prepared analogously starting from compound (75). Compound (71) was prepared analogously starting from compound (70). Compound (82) was prepared analogously starting from compound (81). Compound (84) was prepared analogously starting from compound (83). Compound (86) was prepared analogously starting from compound (85). Compound (88) was prepared analogously starting from compound (87). Compound (90) was prepared analogously starting from compound (89). Compound (92) was prepared analogously starting from compound (91). Compound (94) was prepared analogously starting from compound (93). Compound (96) was prepared analogously starting from compound (95). Compound (98) was prepared analogously starting from compound (97). Compound (100) was prepared analogously starting from compound (99). Compound (102) was prepared analogously starting from compound (101).

Example B.6

Preparation of compound (13)

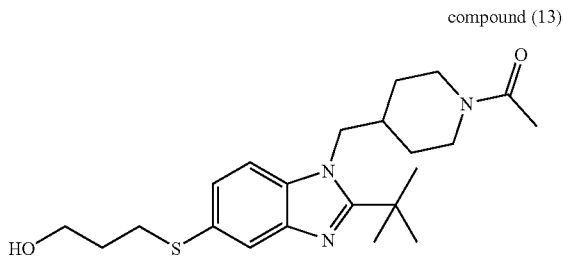

A mixture of intermediate (23) (0.001 mol), 3-bromo-1-propanol (0.003 mol) and Cs$_2$CO$_3$ (0.002 mol) in THF (10 ml)

was stirred for one hour at 60° C. The reaction mixture was cooled, filtered over dicalite and the filtrate's solvent was evaporated. The residue was purified by reversed-phase HPLC. The desired fractions were collected and the solvent was evaporated and co-evaporated to complete dryness, yielding 0.170 g of compound (13).

Compounds (14), (15), (17), (41) and (45) were prepared analogously by reacting intermediate (23) respectively with 1-bromo-2-methoxy-ethane, 3-bromopropanenitrile, 1-(bromomethyl)-4-fluoro-benzene, (bromomethyl)-cyclobutane or 2-bromopropane-nitrile. Compounds (21), (22) and (37) were prepared analogously by reacting intermediate (24) respectively with 1-bromo-3-hydroxy-propane, 1-bromo-2-methoxy-ethane or (bromomethyl)-cyclopropane. Compounds (51), (52), (65), (72), (74) and (75) were prepared analogously by reacting intermediate (23) with 3-pentyl bromide, 2-(4-fluorophenyl)ethyl bromide, 4-heptyl bromide, benzylbromide, 2-propyl iodide or 4-nitrobenzyl bromide respectively in the presence of $K_2CO_3$ in DMF as solvent.

Example B.7

Preparation of compound (18)

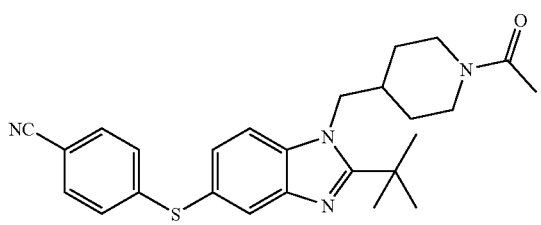

A mixture of intermediate (23) (max. 0.005 mol) and 4-iodobenzonitrile (0.010 mol) in dioxane (80 ml) was degassed and a flow of nitrogen was brought over the reaction mixture (three times). Then $Cs_2CO_3$ (4 g) was added and the mixture was degassed and nitrogen was brought over the reaction mixture again. Then $Pd_2(dba)_3$ (0.200 g) and Xantphos (0.150 g) were added and degassing and the nitrogen action were performed. A nitrogen balloon was left on the reaction mixture and the mixture was stirred overnight at 100° C. The mixture was cooled, filtered and the filtrate was evaporated. The residue was taken up in DCM and washed with water. The separated organic layer was dried ($MgSO_4$), filtered and the solvent was evaporated. The residue was purified by HPLC. The product fractions were collected and the solvent was evaporated, yielding 1.100 g of compound (18).

Compounds (32), (33) and (38) were prepared analogously by reacting intermediate (23) respectively with 1-iodocyclopentane, 4-chloropyridine or 2-bromothiazole. Compounds (54), (57), (58), (66) and (70) were prepared analogously by reacting intermediate (23) respectively with 3-bromopyridine, 2,6-dichloroiodobenzene, 1-fluoro-4-iodobenzene, 2-iodothiophene and 2-chloroiodobenzene. Compound (77) was prepared analogously by reacting intermediate (24) with 2-bromo-thiazole. Compounds (81), (83), (85), (87), (89), (91) and (93) were prepared analogously by reacting intermediate (23) respectively with 1-iodo-3-methoxybenzene, 3-iodo-benzonitrile, intermediate (29), 1-iodo-4-(trifluoromethyl)benzene, 1-chloro-3-iodobenzene, 1-iodo-3-(trifluoromethyl)benzene and 2-iodobenzonitrile. Compounds (95), (97), (99) and (101) were prepared analogously by reacting intermediate (23) respectively with intermediate (30), 3-bromo-N,N-dimethyl-benzenamine, 1-bromo-3-(1-methylethoxy)benzene and 2-iodo-1,3-dimethoxybenzene.

Example B.8

Preparation of compound (28)

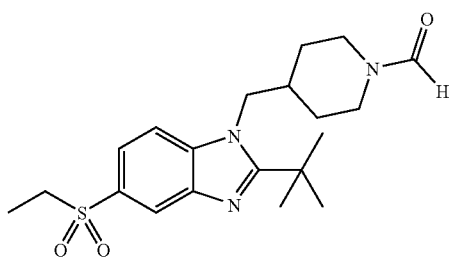

A mixture of intermediate (3) (1.7 g, 0.0047 mol) and methyl formate (25 ml) was reacted overnight at 40° C. The mixture was concentrated at 60° C. under a stream of nitrogen. The residue was crystallized from DIPE with a drop of 2-propanol, yielding 1.55 g of compound (28).

Compound (44) was prepared analogously starting from intermediate (22).

Compound (48) was prepared analogously starting from intermediate (28).

Example B.9

Preparation of compound (29)

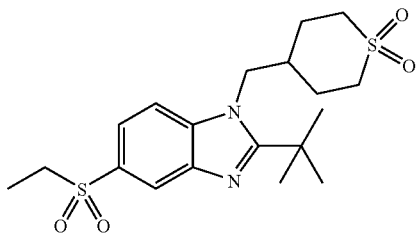

$Cs_2CO_3$ (0.006 mol) was added to a mixture of iodoethane (0.01 mol) in dioxane (15 ml). Then intermediate (27) (0.003 mol) in dioxane (10 ml) was added and the mixture was stirred for 2 hours at 90° C. The reaction mixture was cooled and the solvent was evaporated. The residue was taken up in trichloromethane (50 ml) and then 3-chlorobenzenecarboperoxoic acid (0.018 mol) was added. This reaction mixture was stirred at room temperature for 1 hour. The reaction mixture was washed 2 times with NaOH 1M aqueous solution. The separated organic layer was dried ($MgSO_4$), filtered and the solvent was evaporated. The residue was purified by high-performance liquid chromatography (standard gradient elution with $NH_4HCO_3$ buffer). The product fractions were collected and the solvent was evaporated. This residue was suspended in DIPE and a small amount of $CH_3CN$. The precipitate was filtered off and dried (vacuum, 50° C.), yielding 0.064 g of compound (29) (m.p. 194° C.).

Compounds (30) and (31) were prepared analogously by reacting intermediate (27) respectively with 2-iodo-propane or (bromomethyl)-cyclopropane.

Example B.10

Preparation of

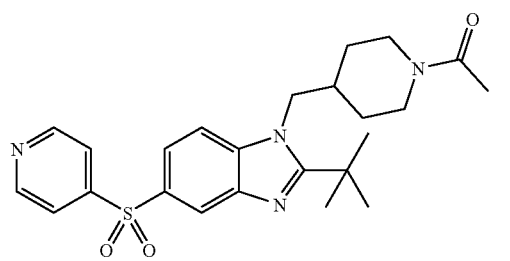
compound (34)

A mixture of 1-{4-[2-tert-butyl-5-(1-oxy-pyridine-4-sulfonyl)-benzoimidazol 1-ylmethyl]-piperidin-1-yl}-ethanone (prepared by oxidizing compound (33) according to the procedure of B.5) and iron in acetic acid were shaken in a closed vessel at 60° C. for 2 hours. The reaction mixture was cooled. The excess of iron was removed by decanting the solvent, which contained the product. The residue of iron was rinsed with 5 ml of acetic acid (again decantation). The combined solvent layers were evaporated. The residue was taken up in DCM and washed with water. The organic layer was dried (MgSO$_4$), filtered and evaporated. The residue was crystallized from DIPE and some 2-propanol. The solid was filtered off, washed and dried, yielding 0.133 g of compound (34).

Example B.11

Preparation of

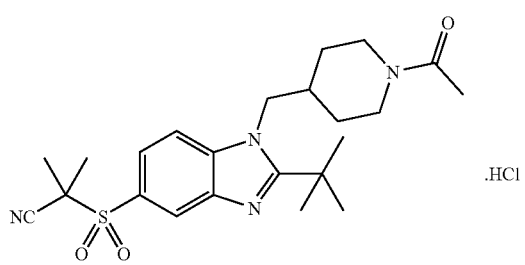
compound (42)
.HCl

Compound (39) and sodium ethoxide in ethanol were degassed and nitrogen was brought over the reaction (in a closed vessel). This mixture was stirred for 15 minutes at room temperature. Iodomethane was added at room temperature and the reaction mixture was stirred for 3 hours. The solvent was concentrated. The residue was taken up in DCM and washed with water. The organic layer was dried with MgSO$_4$, filtered and evaporated. The residue was purified over a column with silica gel using DCM/CH$_3$OH (7N NH$_3$) from 100/0 to 98/2 as eluent. The product fractions were collected and evaporated. The residue was crystallized as an HCl salt, using HCl (1M) in ether and acetonitrile. The solid was filtered off, washed and dried, yielding 0.09 g of compound (42).

Example B.12

Preparation of

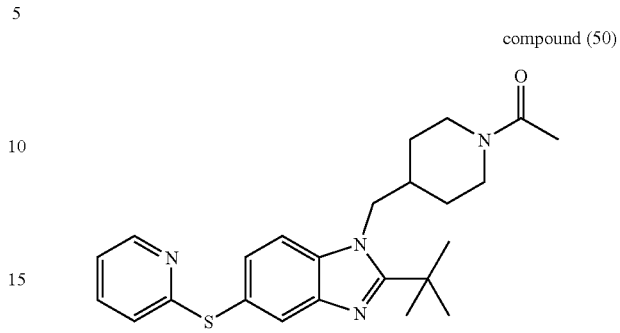
compound (50)

Diisopropylethyl amine (0.003814 mol) and 2-bromopyridine were added to toluene (5 ml). This solution was degassed by putting vacuum and nitrogen atmosphere was brought over it. Then a fresh solution of Xantphos (0.041 g), Pd$_2$(dba)$_3$ (0.0165 g) and dioxane (5 ml) were added with a syringe to the first prepared solution. The reaction was brought under light vacuum. A solution of intermediate (23) in dioxane (5 ml) was also added with a syringe. The reaction mixture was shaken at 84° C. over the weekend. The solvent was evaporated and the product was worked with DCM (40 ml) and water (10 ml). Then the solvent was evaporated. The product was purified with a 40 g silicagel column (eluent: DCM: CH$_3$OH/NH$_3$(7N) from 100/0 to 98/2). The product fractions were put together and the solvent was evaporated until complete dryness, yielding 0.743 g of compound (50).

Example B.13

Preparation of

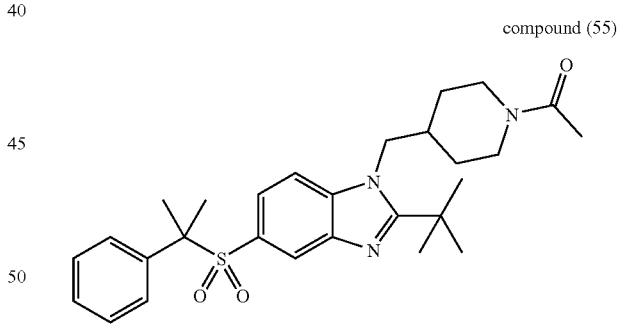
compound (55)

Compound (73) (0.001326 mol) was dissolved in THF (10 ml). The solution was degassed and then the solution was under nitrogen atmosphere. The solution was cooled at 0° C. Then sodium bis(trimethylsylil)amide was added with a syringe. The reaction mixture was stirred during 1 hour at 0° C. Iodomethane (0.947 ml) was added with a syringe to the reaction solution and the reaction mixture was stirred during 1 hour at 0° C. The product was worked up with dichloromethane and water. The organic layer was dried (MgSO$_4$). The solvent was evaporated. The residue was purified using RP HPLC, method B. The fractions were put together and the solvent was evaporated. The product was solidified with DIPE. The solid was filtered off, washed and dried in the oven, yielding 0.165 g of compound (55).

Example B.14

Preparation of compound (16)

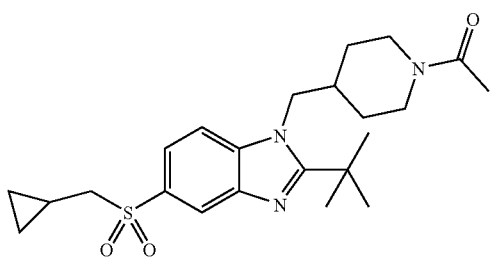

A mixture of intermediate (23) (0.0043 mol), bromomethylcyclopropane (0.01 mol) and $Cs_2CO_3$ (0.008 mol) in THF (10 ml) was degassed. The reaction mixture was stirred at 65° C. for 20 hours under nitrogen. Because some disulfide was formed, $NaBH_4$ was added and the reaction mixture was stirred at 65° C. for another 24 hours. The reaction mixture was filtered to remove the salts. The filtrate was diluted with DCM and washed with water. The organic layer was dried ($MgSO_4$), filtered and evaporated until complete dryness, yielding 2 g of compound (16).

Example B.15

Preparation of compound (78)

Platinum on carbon (5%)+0.5%V (0.3 g) was suspended in THF (50 ml) under nitrogen flow, then compound (69) (0.00157 mol) was added and the reaction mixture was stirred under hydrogen atmosphere until 3 equivalents hydrogen were absorbed. The catalyst was removed by filtration over dicalite and then the solvent was evaporated, yielding 0.839 g of compound (78).

Example B.16

Preparation of compound (79)

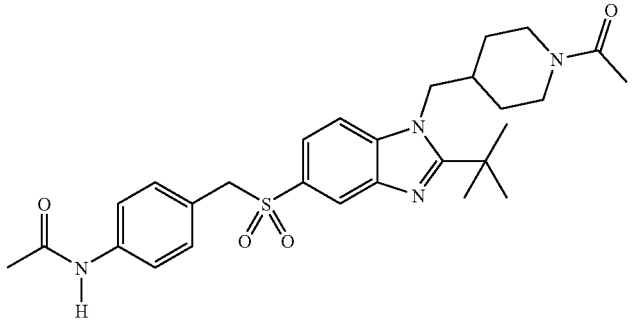

Compound (78) (0.001521 mol) was dissolved in THF (100 ml) and DIPE (0.001521 mol) was added. Acetylchloride (0.001521 mol) was added and the reaction mixture was stirred at room temperature for 30 minutes. Some 1M NaOH solution was added and the product was worked up with THF. The organic layer was dried ($MgSO_4$), filtered off and the solvent was evaporated. The residue was purified according to method A. The fractions were put together and the solvent was evaporated giving 0.375 g of compound (79).

Example B.17

Preparation of compound (80)

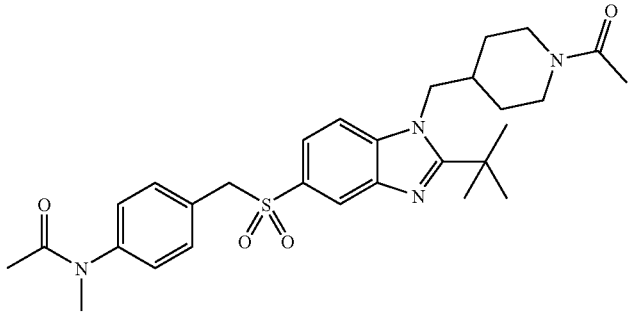

Compound (79) (0.000286 mol) was dissolved in DMF (10 ml). The reaction mixture was cooled at 0° C. under N₂ atmosphere. Then sodium hydride (0.002001 mol; 60% dispersion in mineral oil) was added. The reaction mixture was stirred for 30 minutes and then Iodomethane (0.002573 mol) was added. The reaction mixture was stirred for 1 hour and the product was worked up with dichloromethane (50 ml) and H₂O (20 ml). The organic layer was dried (MgSO₄), filtered off and the solvent was evaporated. The product was solidified with DIPE. The solid was filtered off, washed and dried in the oven, yielding 0.132 g of compound (80).

Table F-1 lists the compounds that were prepared according to one of the above Examples.

TABLE F-1

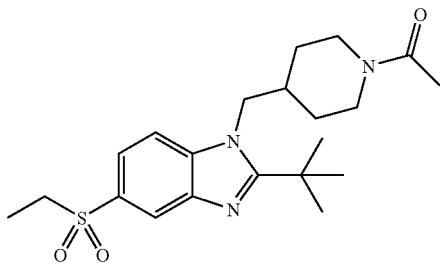

Co. No. 1; Ex. B.1

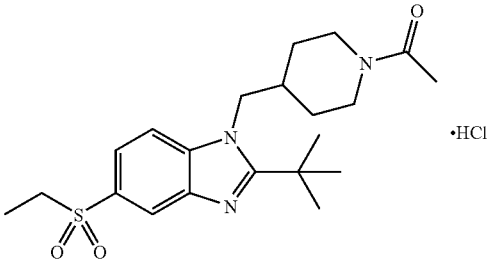

Co. No. 2; Ex. B.1

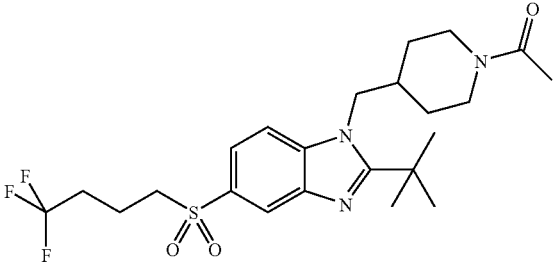

Co. No. 3; Ex. B.2

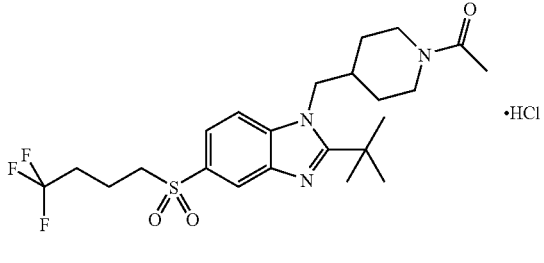

Co. No. 4; Ex. B.3

TABLE F-1-continued

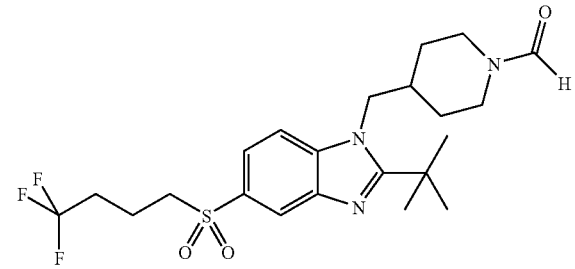

Co. No. 5; Ex. B.4

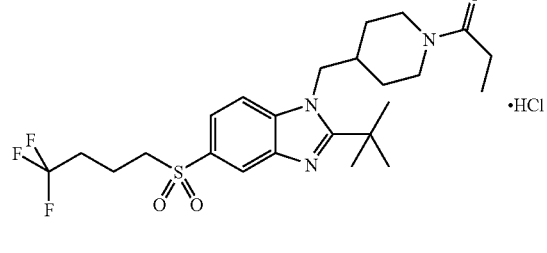

Co. No. 6; Ex. B.3

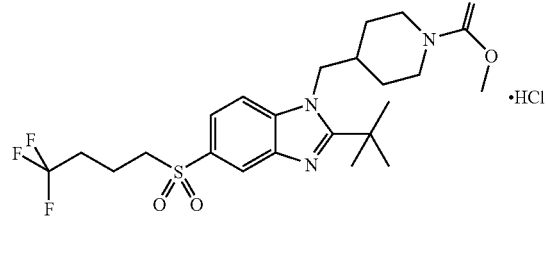

Co. No. 7; Ex. B.3

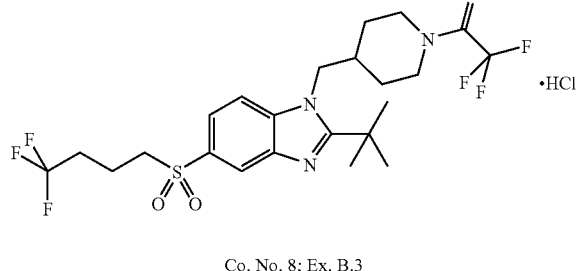

Co. No. 8; Ex. B.3

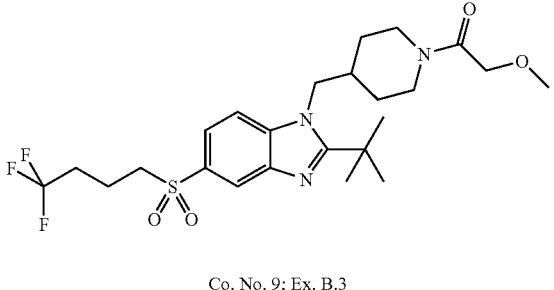

Co. No. 9; Ex. B.3

TABLE F-1-continued
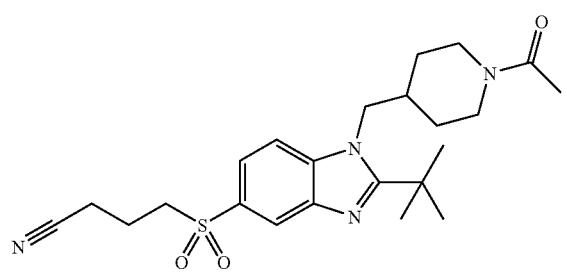
Co. No. 10; Ex. B.2
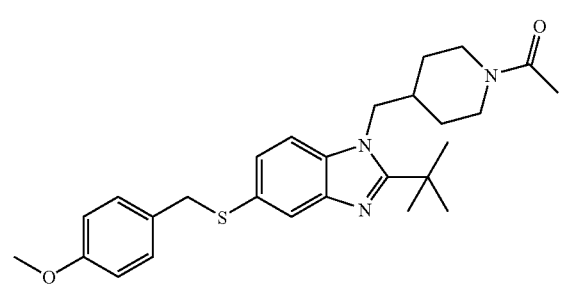
Co. No. 11; Ex. B.3
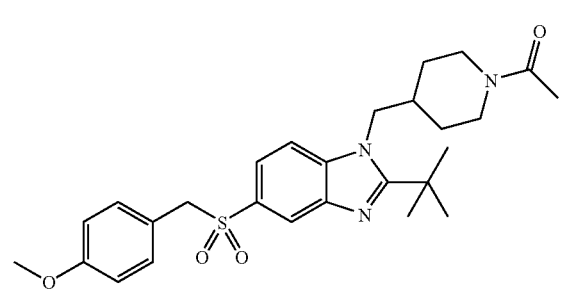
Co. No. 12; Ex. B.5
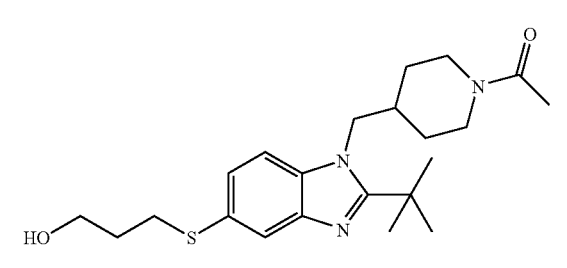
Co. No. 13; Ex. B.6
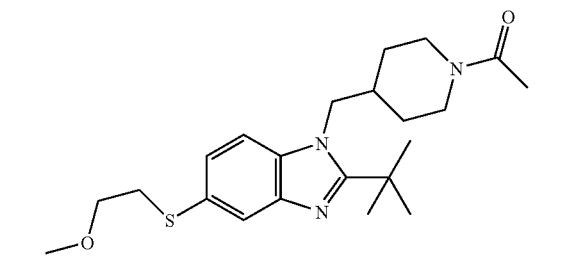
Co. No. 14; Ex. B.6
TABLE F-1-continued
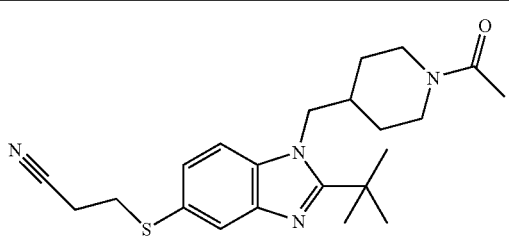
Co. No. 15; Ex. B.6
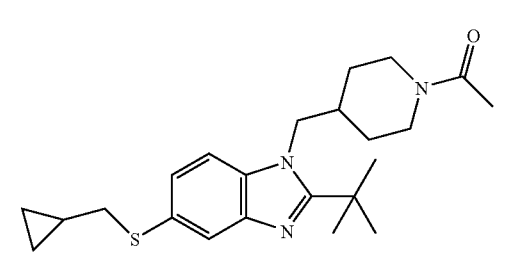
Co. No. 16; Ex. B.14
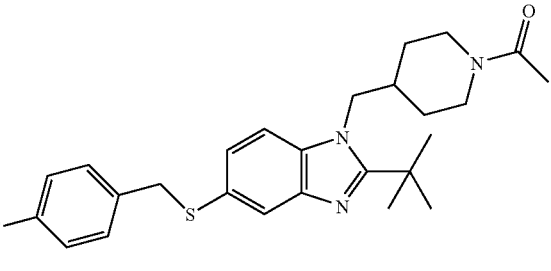
Co. No. 17; Ex. B.6
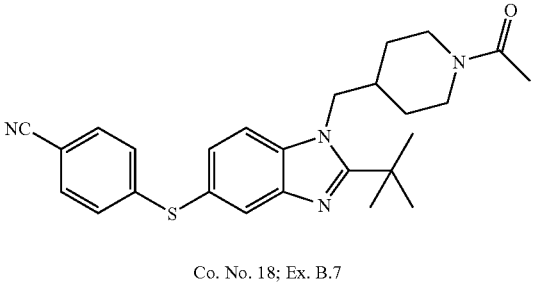
Co. No. 18; Ex. B.7
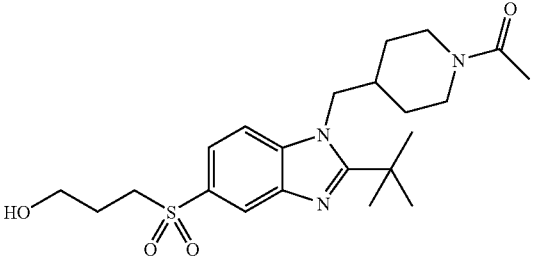
Co. No. 19; Ex. B.5

TABLE F-1-continued
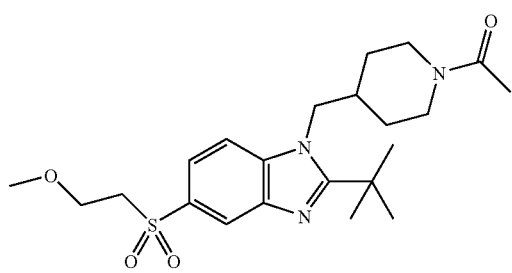
Co. No. 20; Ex. B.5
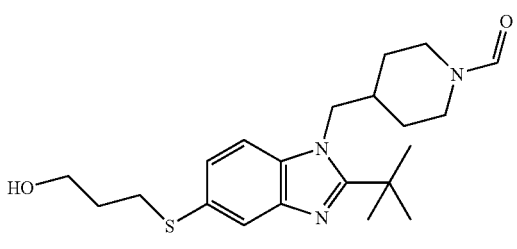
Co. No. 21; Ex. B.6
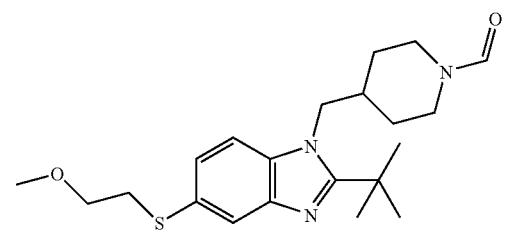
Co. No. 22; Ex. B.6
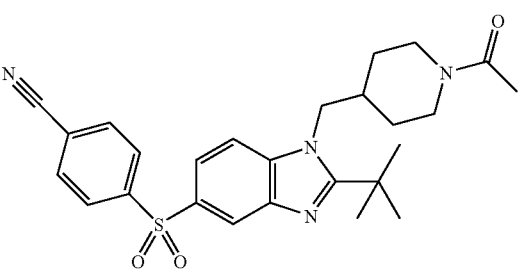
Co. No. 23; Ex. B.5
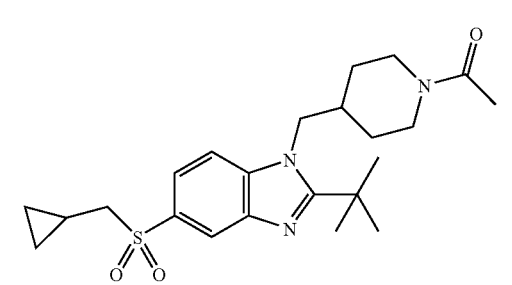
Co. No. 24; Ex. B.5
TABLE F-1-continued
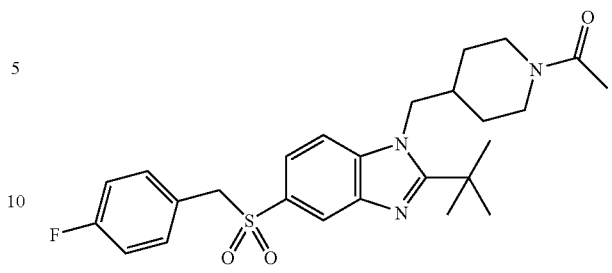
Co. No. 25; Ex. B.5
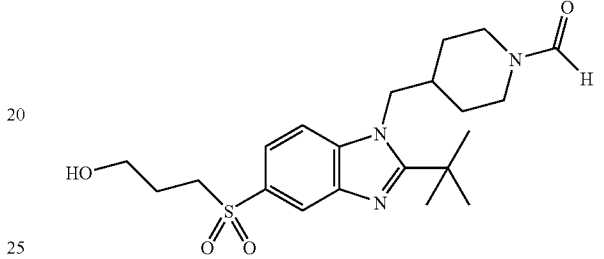
Co. No. 26; Ex. B.5
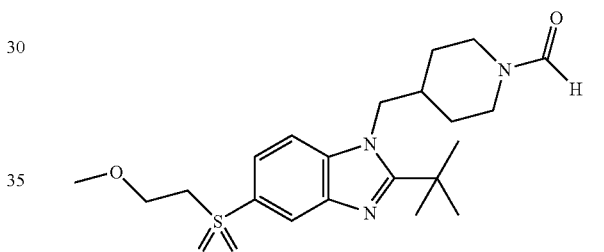
Co. No. 27; Ex. B.5
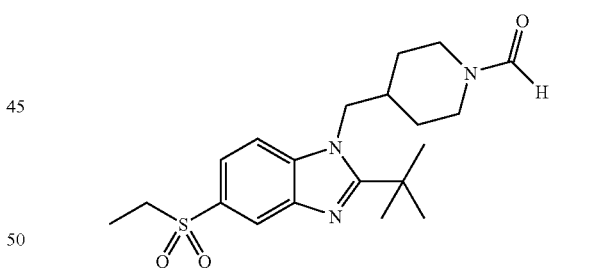
Co. No. 28; Ex. B.8
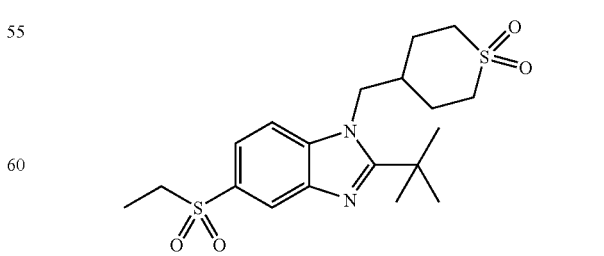
Co. No. 29; Ex. B.9

TABLE F-1-continued
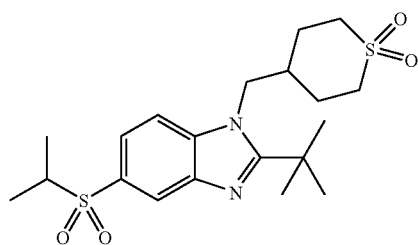
Co. No. 30; Ex. B.9
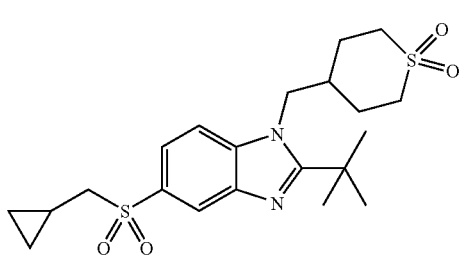
Co. No. 31, Ex. B.9
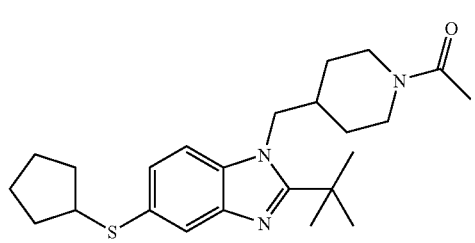
Co. No. 32; Ex. B.7
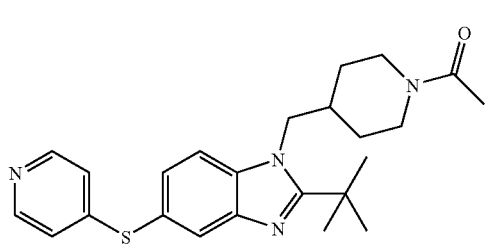
Co. No. 33; Ex. B.7
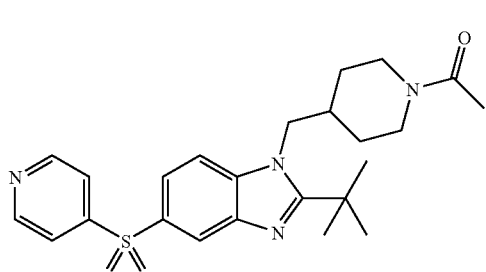
Co. No. 34; Ex. B.10
TABLE F-1-continued
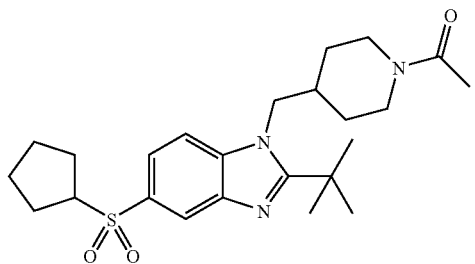
Co. No. 35; Ex. B.5
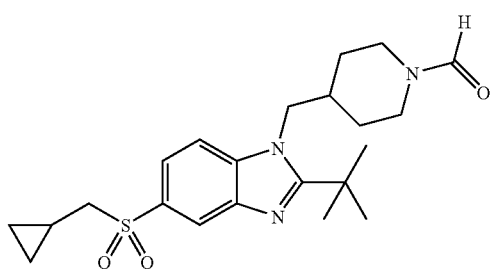
Co. No. 36; Ex. B.5
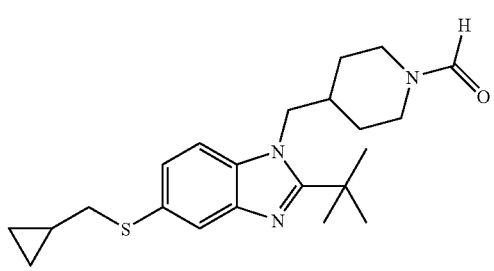
Co. No. 37; Ex. B.6
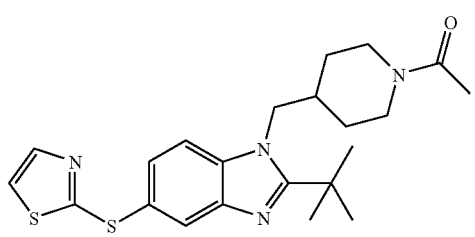
Co. No. 38; Ex. B.7
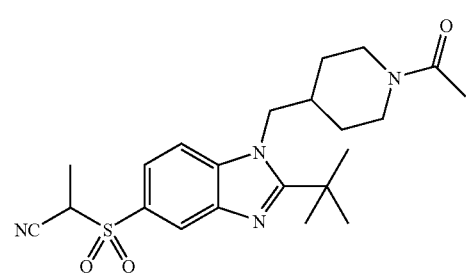
Co. No. 39; Ex. B.5

TABLE F-1-continued
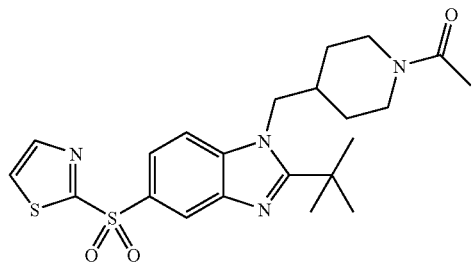
Co. No. 40; Ex. B.5
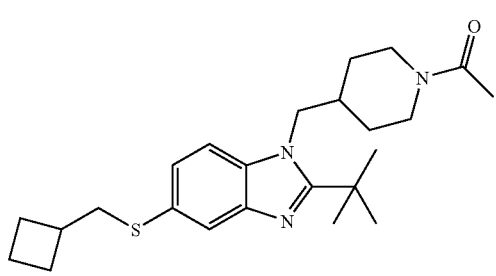
Co. No. 41; Ex. B.6
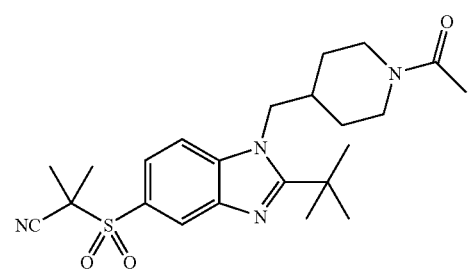
Co. No. 42; Ex. B.11
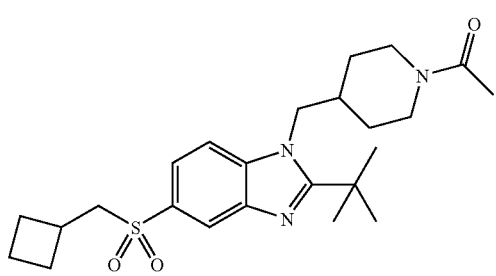
Co. No. 43; Ex. B.5
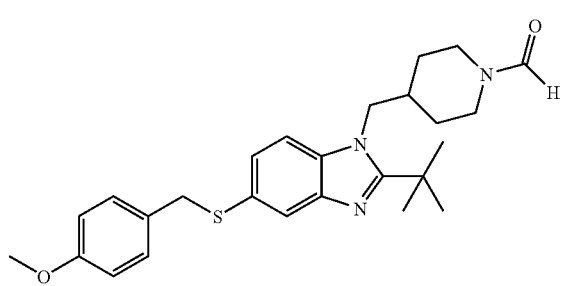
Co. No. 44; Ex. B.8
TABLE F-1-continued
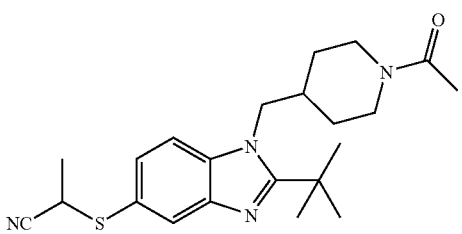
Co. No. 45; Ex. B.6
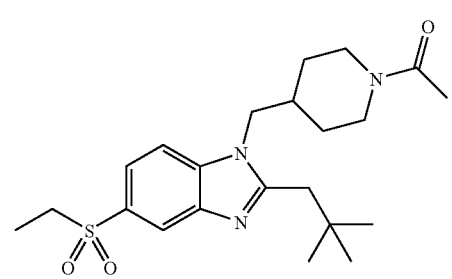
Co. No. 46; Ex. B.1
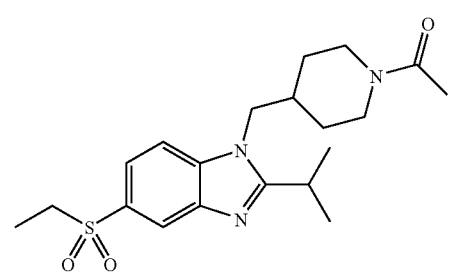
Co. No. 47; Ex. B.2
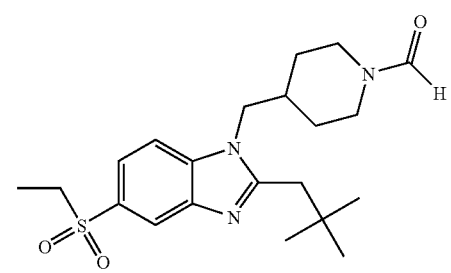
Co. No. 48; Ex. B.8
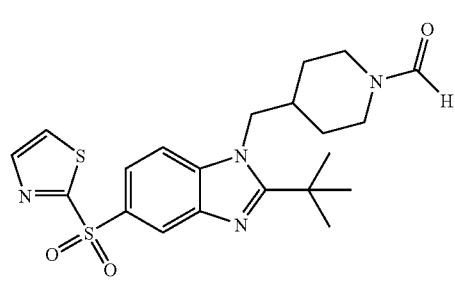
Co. No. 49; Ex. B.5

TABLE F-1-continued
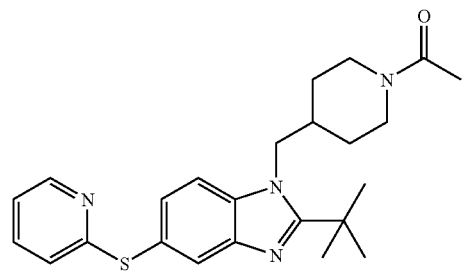
Co. No. 50; Ex. B.12
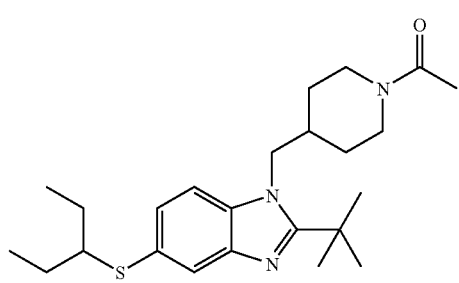
Co. No. 51; Ex. B.6
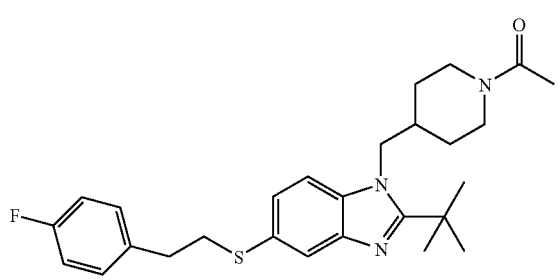
Co. No. 52; Ex. B.6
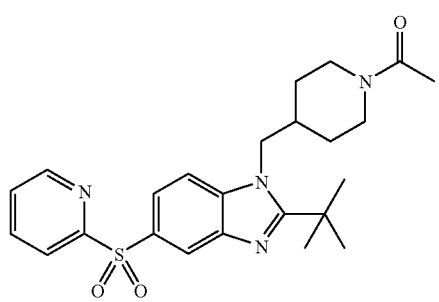
Co. No. 53; Ex. B.5
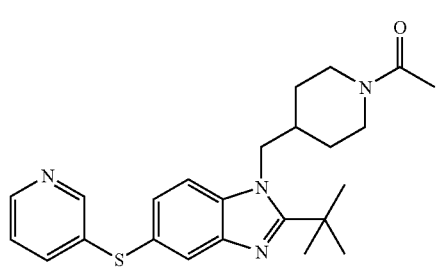
Co. No. 54; Ex. B.7
TABLE F-1-continued
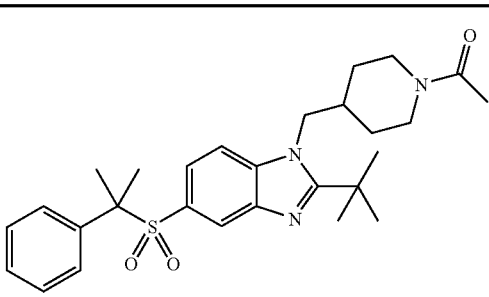
Co. No. 55; Ex. B.13
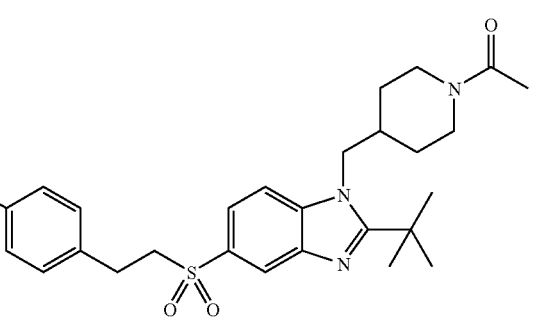
Co. No. 56; Ex. B.5
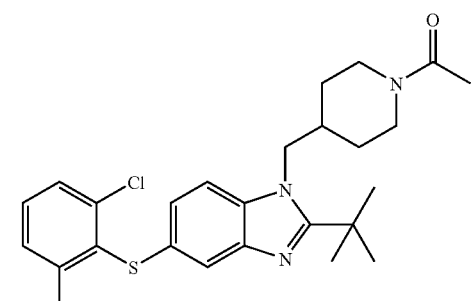
Co. No. 57; Ex. B.7
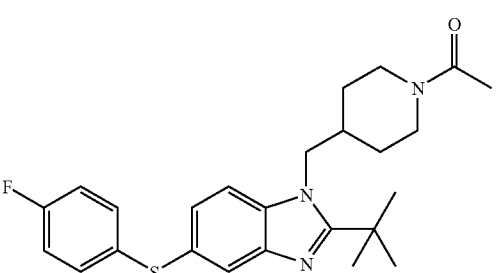
Co. No. 58; Ex. B.7

TABLE F-1-continued
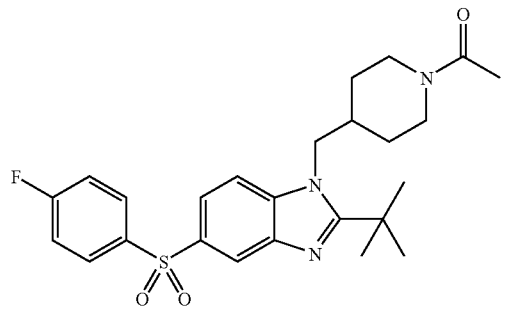
Co. No. 59; Ex. B.5
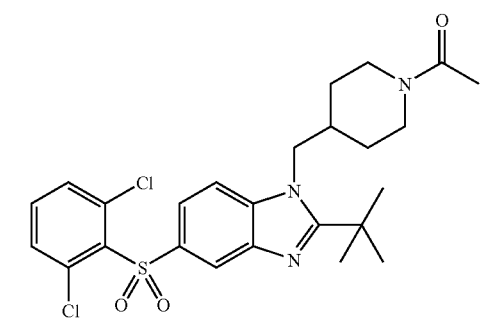
Co. No. 60; Ex. B.5
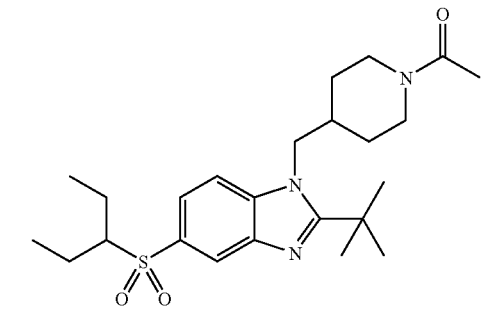
Co. No. 61; Ex. B.5
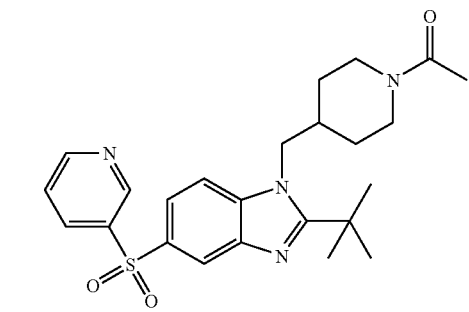
Co. No. 62; Ex. B.5
TABLE F-1-continued
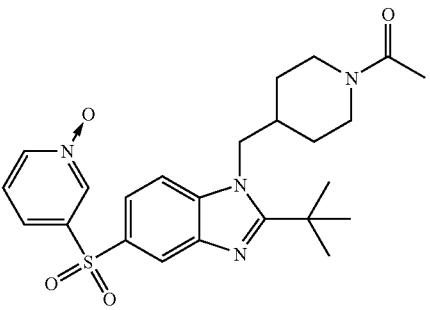
Co. No. 63; Ex. B.5
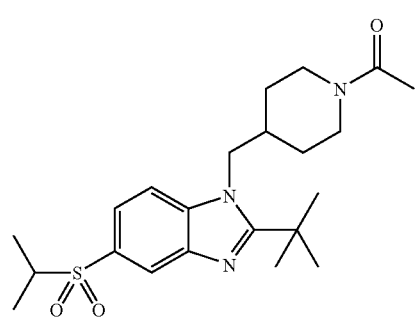
Co. No. 64; Ex. B.5
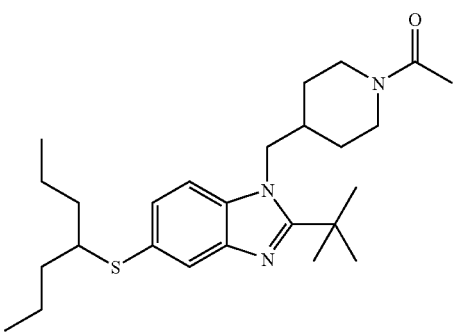
Co. No. 65; Ex. B.6
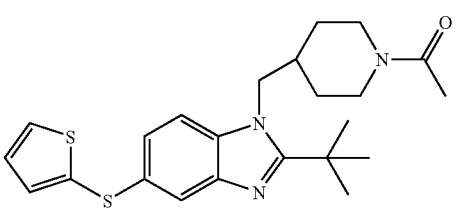
Co. No. 66; Ex. B.7

TABLE F-1-continued
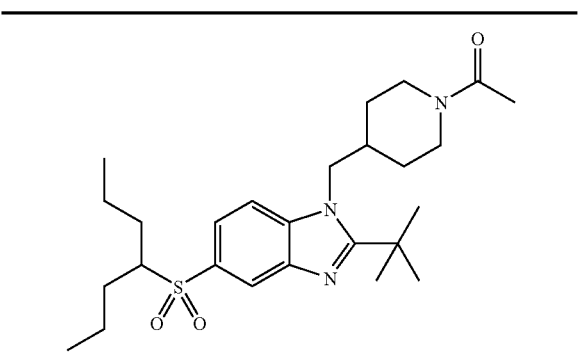
Co. No. 67; Ex. B.5
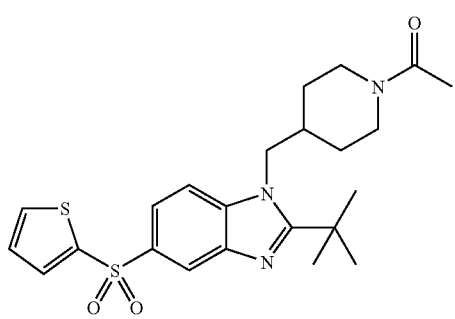
Co. No. 68; Ex. B.5
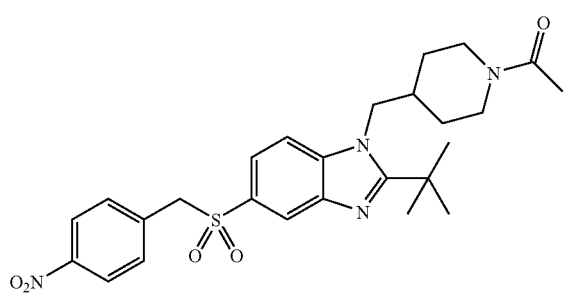
Co. No. 69; Ex. B.7
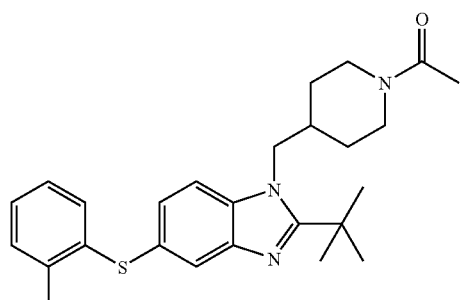
Co. No. 70; Ex. B.7
TABLE F-1-continued
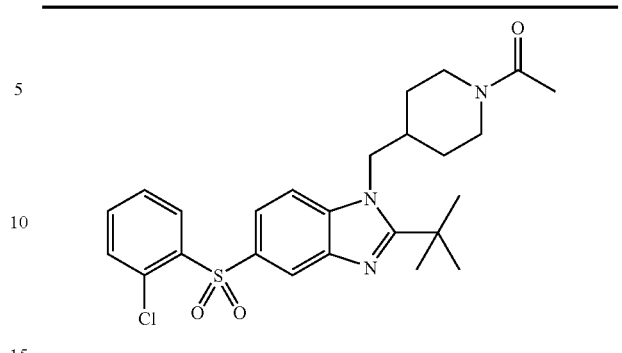
Co. No. 71; Ex. B.5
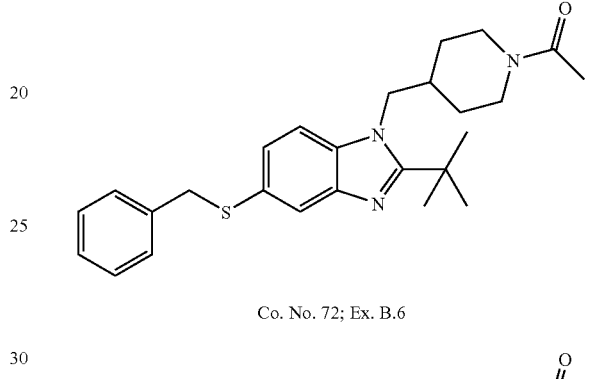
Co. No. 72; Ex. B.6
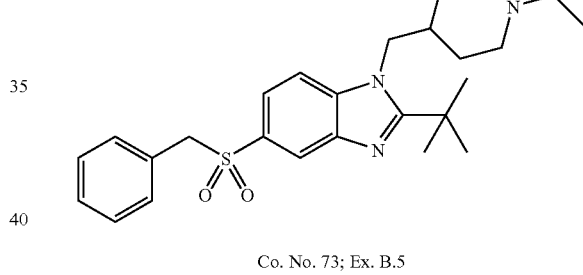
Co. No. 73; Ex. B.5
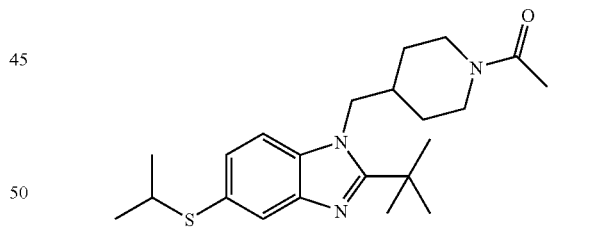
Co. No. 74; Ex. B.6
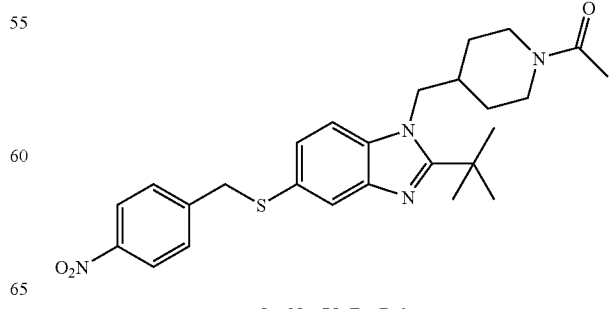
Co. No. 75; Ex. B.6

TABLE F-1-continued
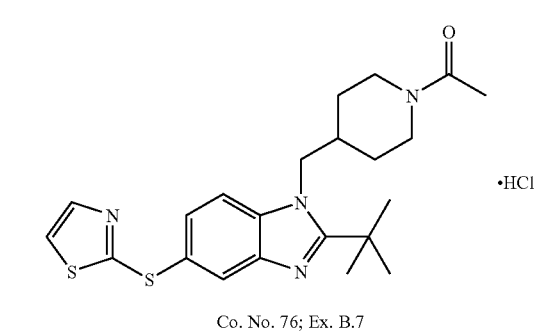
Co. No. 76; Ex. B.7
·HCl
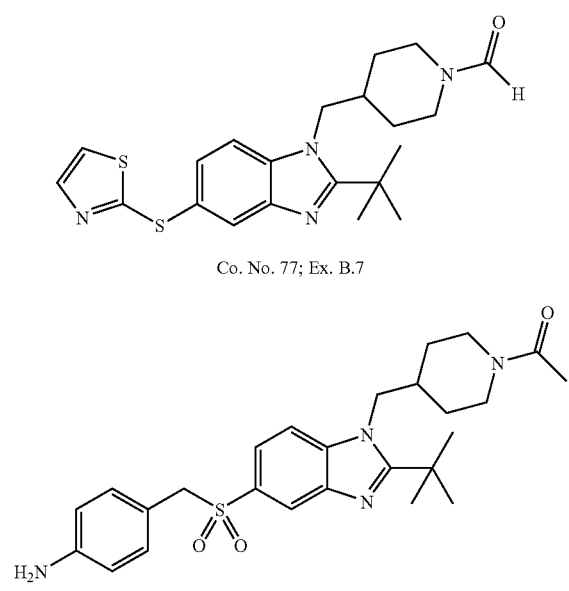
Co. No. 77; Ex. B.7
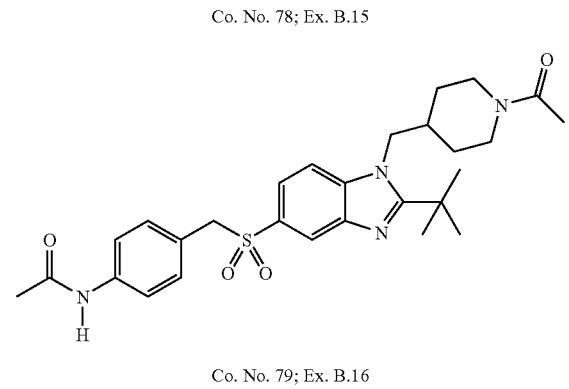
Co. No. 78; Ex. B.15
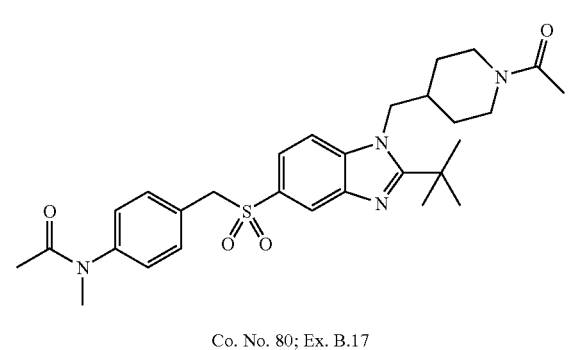
Co. No. 79; Ex. B.16
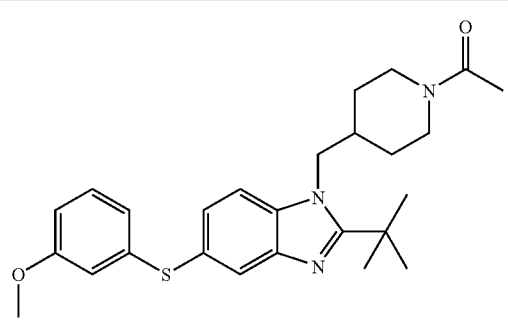
Co. No. 80; Ex. B.17
TABLE F-1-continued
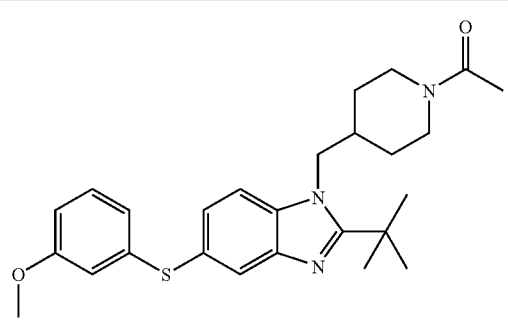
Co. No. 81; Ex. B.7
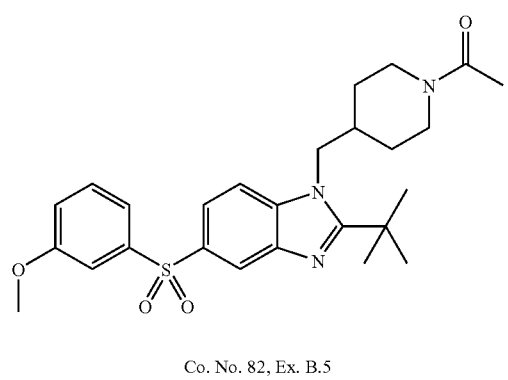
Co. No. 82, Ex. B.5
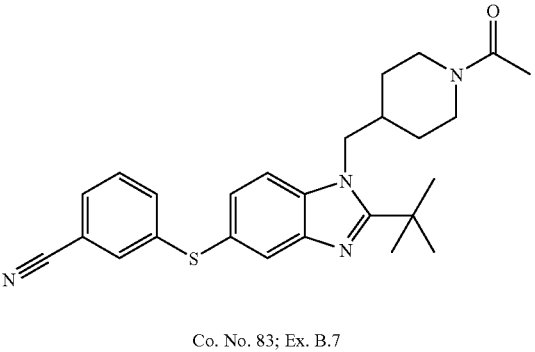
Co. No. 83; Ex. B.7
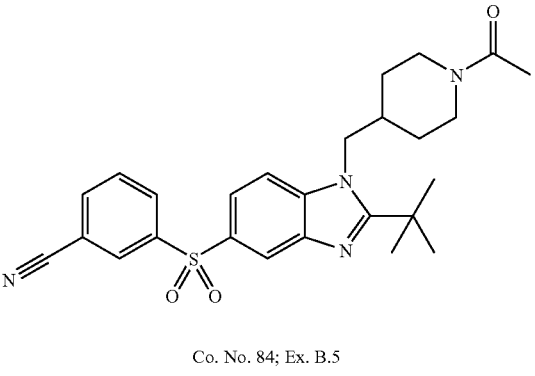
Co. No. 84; Ex. B.5

TABLE F-1-continued
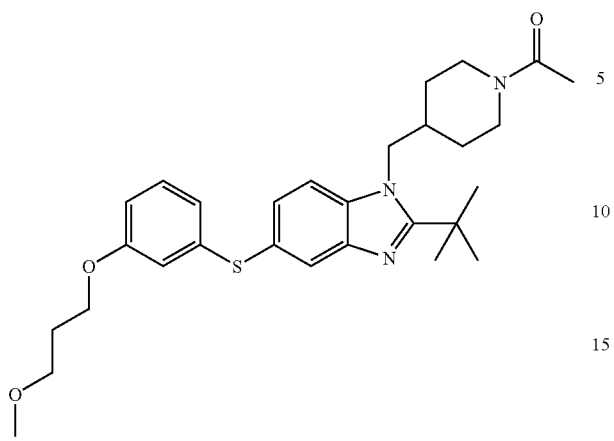
Co. No. 85; Ex. B.7
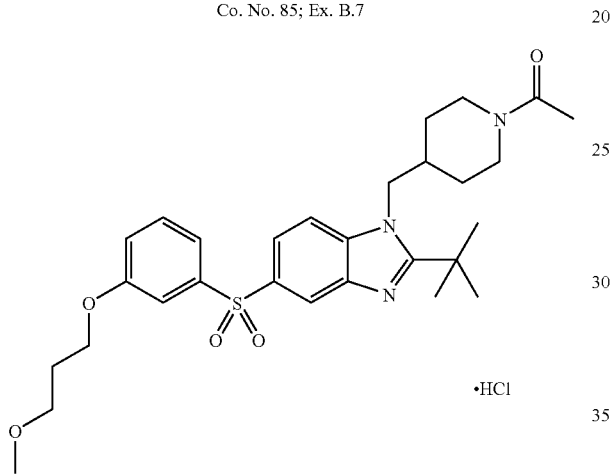
•HCl
Co. No. 86; Ex. B.5
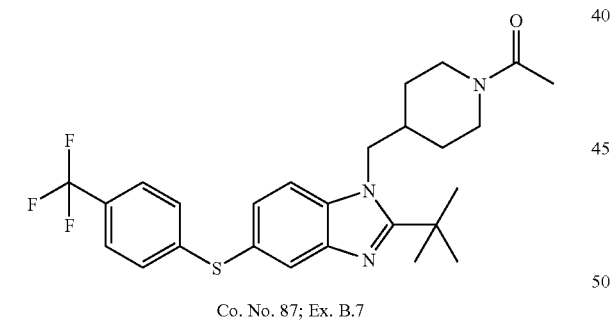
Co. No. 87; Ex. B.7
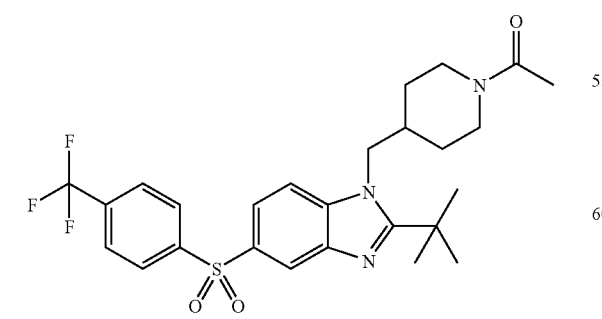
Co. No. 88; Ex. B.5
TABLE F-1-continued
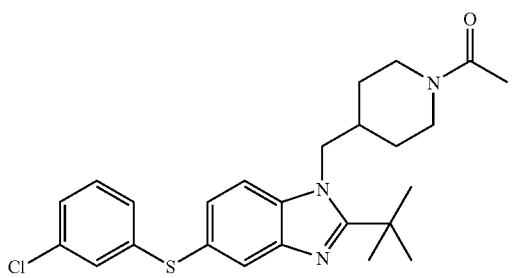
Co. No. 89; Ex. B.7
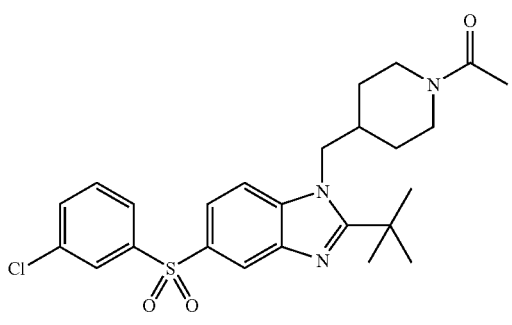
Co. No. 90; Ex. B.5
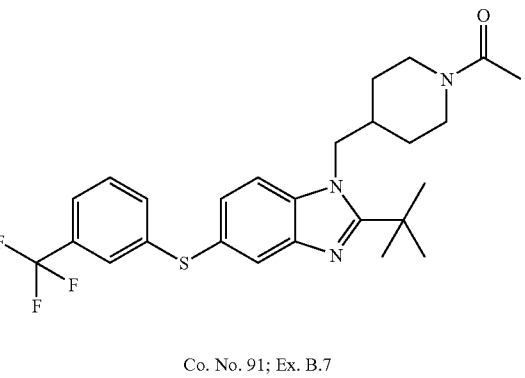
Co. No. 91; Ex. B.7
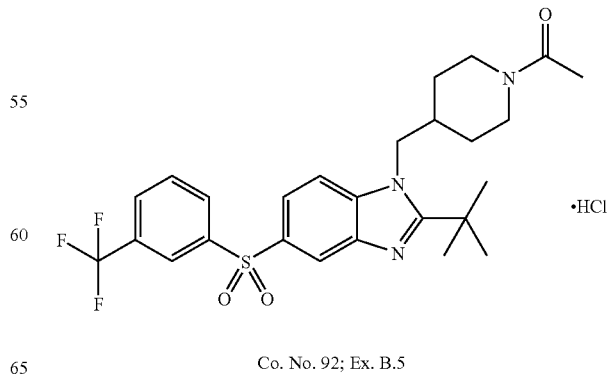
•HCl
Co. No. 92; Ex. B.5

TABLE F-1-continued
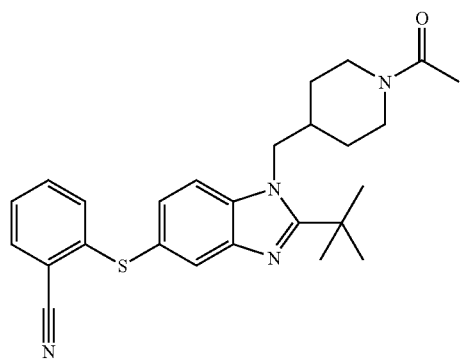
Co. No. 93; Ex. B.7
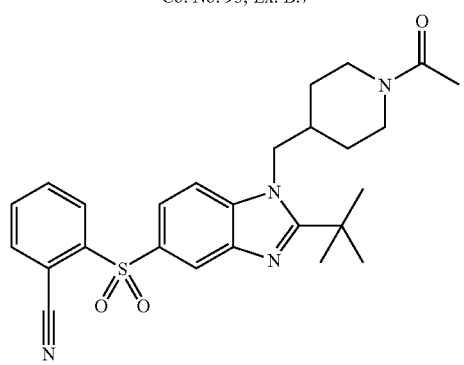
Co. No. 94; Ex. B.5
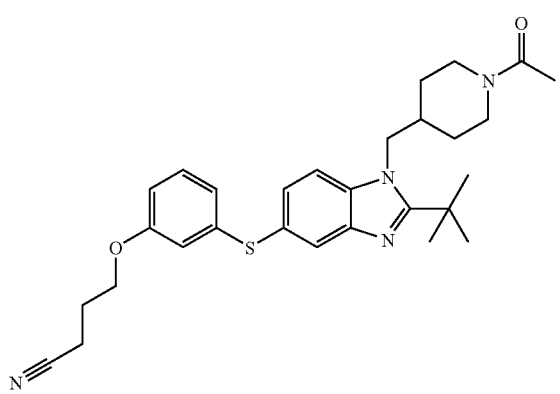
Co. No. 95; Ex. B.7
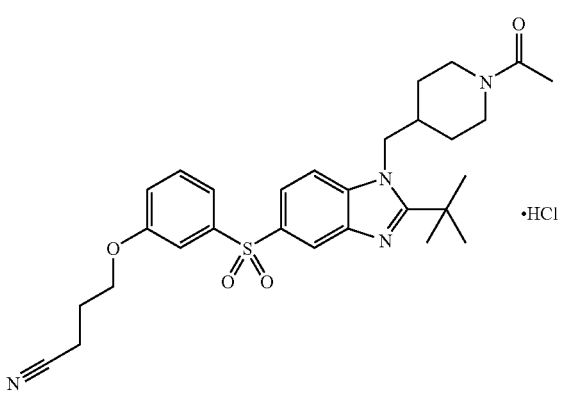
Co. No. 96; Ex. B.5
TABLE F-1-continued
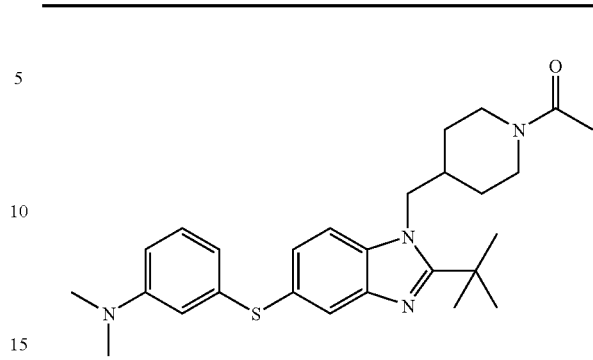
Co. No. 97; Ex. B.7
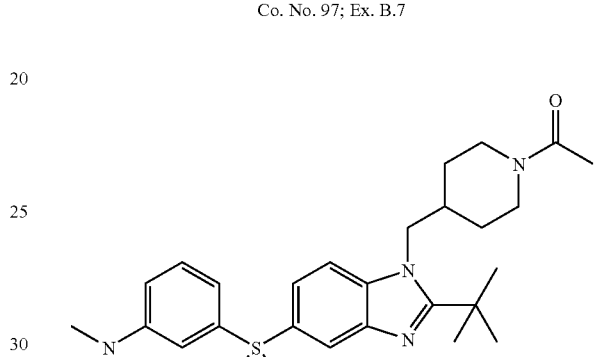
Co. No. 98; Ex. B.5
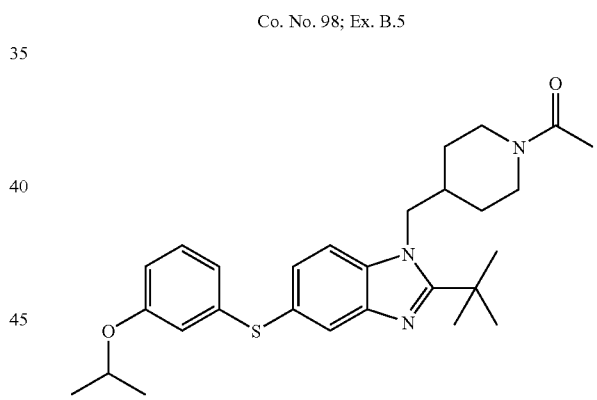
Co. No. 99; Ex. B.7
·HCl
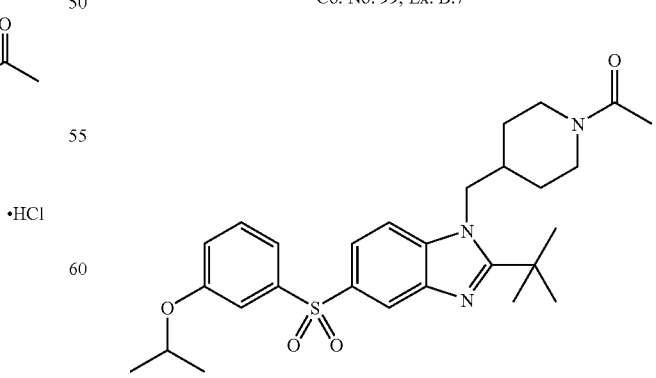
Co. No. 100; Ex. B.5

TABLE F-1-continued
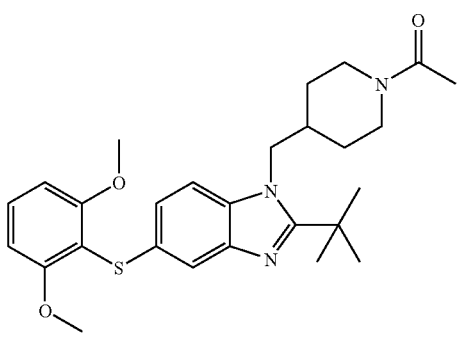
Co. No. 101; Ex. B.7
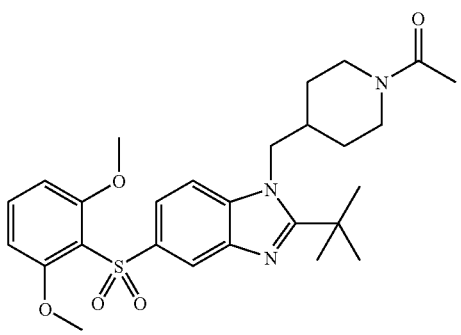
Co. No. 102; Ex. B.5
Table F-2 lists the compounds that were prepared using the procedures as described in Examples B.5 and B.7, and for compound (116) further treatment with Fe/acetic acid as described in Example B.10.
TABLE F-2
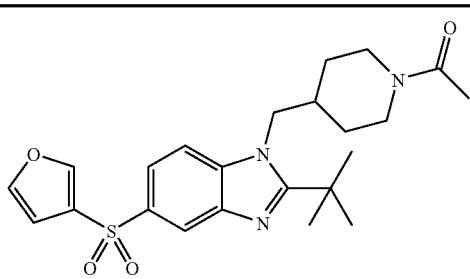
Co. No. 103
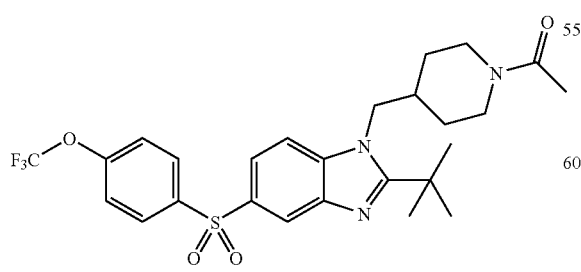
Co. No. 104
TABLE F-2-continued
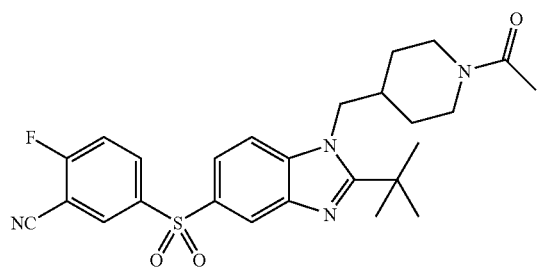
Co. No. 105
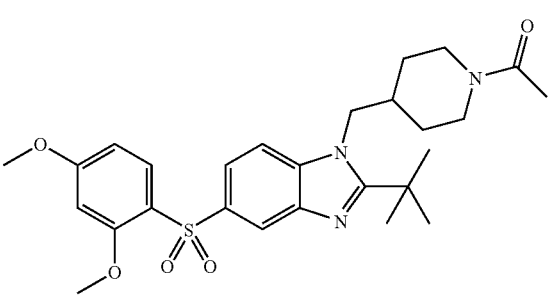
Co. No. 106
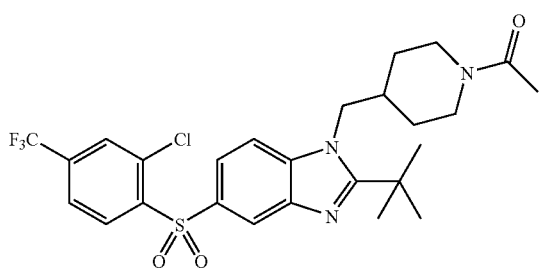
Co. No. 107
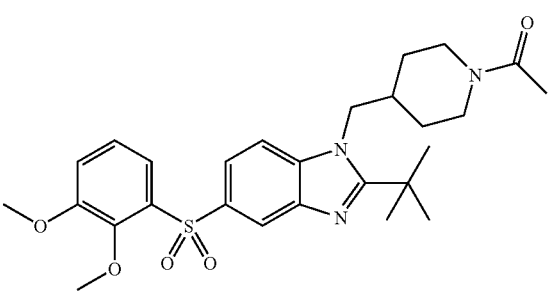
Co. No. 108
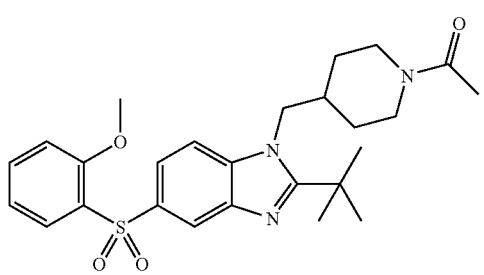
Co. No. 109

TABLE F-2-continued

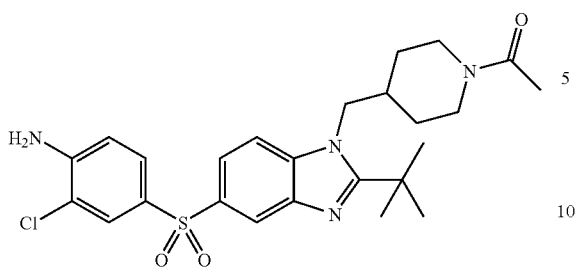

Co. No. 110

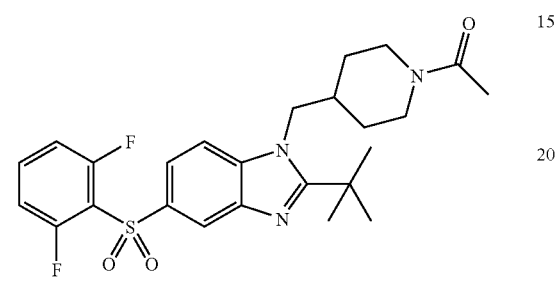

Co. No. 111

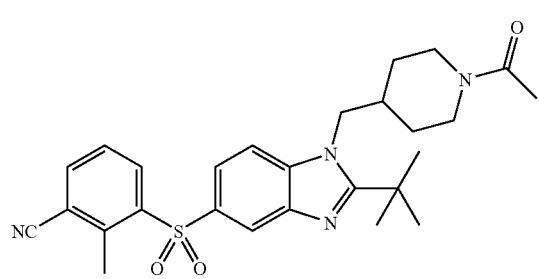

Co. No. 112

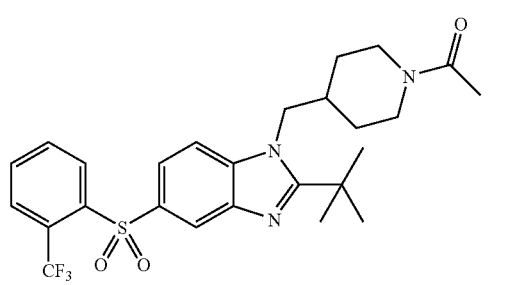

Co. No. 113

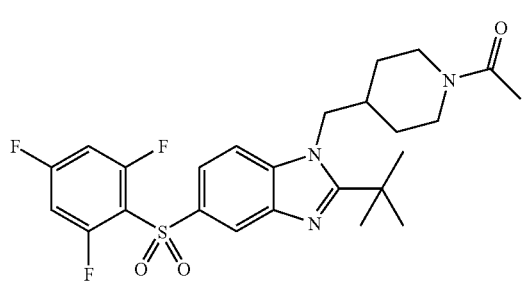

Co. No. 114

TABLE F-2-continued

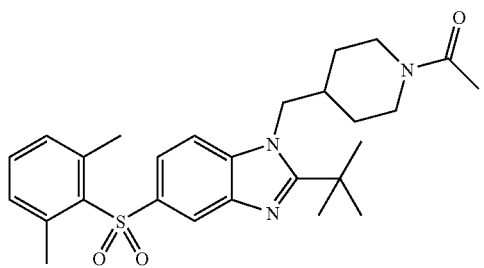

Co. No. 115

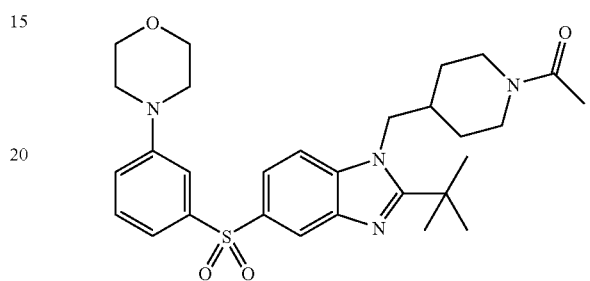

Co. No. 116

C. Compound Identification

C1. LCMS

For LCMS-characterization of the compounds of the present invention, the following methods were used.

General Procedure A

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General Procedure B

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

LCMS Procedure 1

In addition to general procedure A: Reversed phase HPLC was carried out on an Xterra MS C18 column (3.5 μm, 4.6× 100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS Procedure 2

In addition to general procedure B: Reversed phase HPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (mobile phase A: 0.1% formic acid in $H_2O$/methanol 95/5; mobile phase B: methanol) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

LCMS Procedure 3

In addition to general procedure A: Column heater was set at 45° C. Reversed phase HPLC was carried out on an Xterra MS C18 column (3.5 μm, 4.6×100 mm) with a flow rate of 1.6 ml/min. Three mobile phases (mobile phase A: 0.1% formic acid in $H_2O$/methanol 95/5; mobile phase B: acetonitrile; mobile phase C: methanol) were employed to run a gradient condition from 100% A to 1% A, 49% B and 50% C in 7 minutes and hold these conditions for 1 minute. An injection volume of 10 μl was used. Cone voltage was 10 V for positive ionization mode.

LCMS Procedure 4

In addition to general procedure A: Column heater was set at 60° C. Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute and hold these conditions for 1 minute and reequilibrate with 100% A for 1.5 minutes. An injection volume of 10 μl was used. Cone voltage was 10 V for positive ionization mode and 20 V for negative ionization mode.

LCMS Procedure 5

In addition to general procedure A: Reversed phase HPLC was carried out on an Atlantis C18 column (3.5 μm, 4.6×100 mm) with a flow rate of 1.6 ml/min. Two mobile phases (mobile phase A: 70% methanol+30% $H_2O$; mobile phase B: 0.1% formic acid in $H_2O$/methanol 95/5) were employed to run a gradient condition from 100% B to 5% B+95% A in 12 minutes. An injection volume of 10 μl was used. Cone voltage was 10 V for positive ionization mode and 20 V for negative ionization mode.

C2. Melting Points

For a number of compounds, melting points were determined with a DSC823e (Mettler-Toledo). Melting points were measured with a temperature gradient of 30° C./minute. Reported values are peak values. Maximum temperature was 400° C.

For a number of compounds, melting points were obtained with a Kofler hot bench, consisting of a heated plate with linear temperature gradient, a sliding pointer and a temperature scale in degrees Celsius.

TABLE C1

| Co. No. | $R_t$ | $(MH)^+$ | Procedure | Physico-chemical data |
|---|---|---|---|---|
| 1 | 4.42 | 406 | 1 | — |
| 2 | 4.41 | 406 | 1 | mp: >100° C. (sticky) (Kofler) |
| 3 | 1.09 | 488 | 2 | — |
| 4 | 5.22 | 488 | 1 | mp: >100° C. (sticky) (Kofler) |
| 5 | 1.06 | 474 | 2 | mp: >100° C. (sticky) (Kofler) |
| 6 | 1.14 | 502 | 2 | mp: >100° C. (sticky) (Kofler) |
| 7 | 1.19 | 504 | 2 | mp: >100° C. (sticky) (Kofler) |
| 8 | 1.22 | 542 | 2 | mp: >100° C. (sticky) (Kofler) |
| 9 | 1.09 | 518 | 2 | mp: >100° C. (sticky) (Kofler) |
| 10 | 0.88 | 445 | 2 | — |
| 11 | 6.10 | 466 | 1 | — |
| 12 | 1.07 | 498 | 2 | — |
| 13 | 0.74 | 404 | 2 | — |
| 14 | 0.80 | 404 | 2 | — |
| 15 | 0.75 | 399 | 2 | — |
| 16 | 0.97 | 400 | 2 | — |
| 17 | 6.13 | 454 | 1 | — |
| 18 | 1.14 | 447 | 2 | — |
| 19 | 3.98 | 436 | 1 | — |
| 20 | 4.35 | 436 | 1 | — |
| 21 | 4.58 | 390 | 1 | — |
| 22 | 0.76 | 390 | 2 | — |
| 23 | 1.07 | 479 | 2 | — |
| 24 | 0.99 | 432 | 2 | mp: 150° C. (DSC) |
| 25 | 5.21 | 486 | 1 | mp: >100° C. (sticky) (Kofler) |
| 26 | 3.51 | 422 | 4 | mp: >100° C. (sticky) (Kofler) |
| 27 | 3.85 | 422 | 4 | mp: >100° C. (sticky) (Kofler) |
| 28 | 4.29 | 392 | 1 | mp: 188-190° C. (Kofler) |
| 29 | 3.67 | 413 | 4 | mp: 194° C. (Kofler) |
| 30 | 0.89 | 427 | 2 | — |
| 31 | 4.38 | 439 | 1 | mp: 234° C. (DSC) |
| 32 | 1.08 | 414 | 2 | — |
| 33 | 0.79 | 423 | 2 | — |
| 34 | 1.00 | 455 | 2 | mp: 179° C. (DSC) |
| 35 | 1.07 | 446 | 2 | — |
| 36 | 4.54 | 418 | 1 | mp: 186° C. (DSC) |
| 37 | 5.72 | 386 | 1 | — |
| 38 | 0.99 | 429 | 2 | — |
| 39 | 0.98 | 431 | 2 | — |
| 40 | 1.04 | 461 | 2 | mp: 191° C. (DSC) |
| 41 | 1.09 | 414 | 2 | — |
| 42 | 1.05 | 445 | 2 | — |
| 43 | 5.11 | 446 | 1 | mp: 155° C. (DSC) |
| 45 | 0.91 | 399 | 2 | — |
| 46 | 4.91 | 420 | 1 | mp: 152-155° C. (Kofler) |
| 47 | 4.00 | 392 | 1 | mp: unclear, foamy sticky solid (Kofler) |
| 48 | 4.81 | 406 | 1 | mp: 166-168° C. (Kofler) |
| 49 | 4.71 | 447 | 3 | mp: 190° C. (DSC) |
| 50 | 0.93 | 423 | 2 | — |
| 51 | 1.15 | 416 | 2 | — |
| 52 | 1.13 | 468 | 2 | — |
| 53 | 0.96 | 455 | 2 | mp: 205° C. (DSC) |
| 54 | 0.93 | 423 | 2 | — |
| 55 | 1.18 | 496 | 2 | — |
| 56 | 1.16 | 500 | 2 | — |
| 57 | 1.20 | 490 | 2 | — |
| 58 | 1.14 | 440 | 2 | — |
| 59 | 1.13 | 472 | 2 | mp: 186° C. (DSC) |
| 60 | 1.18 | 522 | 2 | mp: 224° C. (DSC) |
| 61 | 1.14 | 448 | 2 | — |
| 62 | 1.00 | 455 | 2 | — |
| 63 | 0.92 | 471 | 2 | — |
| 65 | 1.34 | 444 | 2 | — |
| 66 | 1.12 | 428 | 2 | — |
| 67 | 1.27 | 476 | 2 | mp: 132° C. (DSC) |
| 68 | 1.07 | 460 | 2 | mp: 187° C. (DSC) |
| 69 | 1.10 | 513 | 2 | — |
| 70 | 1.23 | 456 | 2 | — |
| 71 | 1.12 | 488 | 2 | mp: 218° C. (DSC) |
| 72 | 6.85 | 436 | 5 | — |
| 72 | 0.98 | 420 | 2 | — |
| 73 | 1.08 | 468 | 2 | — |
| 75 | 1.04 | 481 | 2 | — |
| 76 | 4.21 | 429 | 3 | — |
| 77 | 0.96 | 415 | 2 | — |

TABLE C1-continued

Analytical data

| Co. No. | $R_t$ | $(MH)^+$ | Procedure | Physico-chemical data |
|---|---|---|---|---|
| 78 | 0.84 | 483 | 2 | — |
| 79 | 4.12 | 525 | 4 | — |
| 80 | 1.08 | 567 | 2 | — |
| 81 | 1.13 | 452 | 2 | — |
| 82 | 1.14 | 484 | 2 | mp: 164° C. (DSC) |
| 83 | 1.12 | 447 | 2 | — |
| 84 | 1.08 | 479 | 2 | mp: 191° C. (DSC) |
| 85 | 1.20 | 510 | 2 | — |
| 86 | 1.20 | 542 | 2 | — |
| 87 | 1.34 | 490 | 2 | — |
| 88 | 1.26 | 522 | 2 | mp: 189° C. (DSC) |
| 89 | 1.30 | 456 | 2 | — |
| 90 | 1.23 | 488 | 2 | mp: 192° C. (DSC) |
| 91 | 1.32 | 490 | 2 | — |
| 92 | 1.25 | 522 | 2 | — |
| 93 | 1.06 | 447 | 2 | — |
| 94 | 1.09 | 479 | 2 | — |
| 95 | 1.09 | 505 | 2 | — |
| 96 | 1.09 | 537 | 2 | — |
| 97 | 1.14 | 465 | 2 | — |
| 98 | 5.18 | 497 | 4 | — |
| 99 | 1.25 | 480 | 2 | — |
| 100 | 1.27 | 512 | 2 | — |
| 101 | 0.92 | 482 | 2 | — |
| 102 | 1.00 | 514 | 2 | — |

D. Pharmacological Examples

D.1 Inhibition of cAMP in Response to Activation of the Human CB2 Receptors

Functional activity of the test compounds was assessed by measuring their potency to inhibit forskolin-activated cAMP production upon activation of human CB2 (hCB2) receptor through homogenous time resolved fluorescence (HTRF) assays.

CHO-K1 cells stably transfected with hCB2 were grown up to 80-90% confluence in T175 Falcon flasks in DMEM/NUT MIX F-12 culture medium complemented with 2% Solution A ($5.10^6$ IU/l penicillin G, 5 g/l streptomycin sulphate, 5.5 g/l pyruvate, 14.6 g/l L-glutamine, 1M NaOH) and 10% foetal calf serum. Before the experiments, medium was removed, cells were washed with PBS/EDTA (140 mM NaCl, 1 mM $Na_2$-EDTA, 8 mM $Na_2HPO_4.2H_2O$, 8.5 mM $KH_2PO_4$, 2.7 mM KCl, 21 mM glucose), resuspended in stimulation buffer (HBSS 1×, IBMX 1 mM, Hepes 5 mM, $MgCl_2$ 10 mM, BSA 0.1%, pH 7.4). Cells were diluted to a concentration of $10^6$ cells/ml for hCB2 experiments. Assays were performed using the cAMP Dynamic HTRF kit (CIS bio international, France) according to the recommendations of the manufacturer.

For CB2, each well of a 384 flat bottom black polystyrene assay plate (Costar) was filled with 10 µl stimulation buffer containing 15 µM forskolin and either test compound (in 3% DMSO), 3% DMSO or 10 µM Win55212-2 (in 3% DMSO). Then, 20 µl of the diluted hCB2-CHO-K1 cells was added (20,000 cells/well). After 30 minutes incubation in dark at room temperature, 10 µl cAMP-XL665 and 10 µl anti-cAMP cryptate (both at a final dilution of 1/100) was added to the cells.

After equilibration of the reaction mixtures for 1 to 24 hours in dark at room temperature, fluorescence was measured at 665 nm and 620 nm using a Discovery microplate fluorescence counter (Perkin Elmer), and the signal ratio of 665 nm/620 nm was calculated. The signal ratios of the test compounds were expressed relative to the signal ratios of the DMSO control (maximal signal ratio, no inhibition of cAMP) and WIN55212-2 for hCB2, respectively (minimal signal ratio, maximal inhibition of cAMP). From the dose response curves generated for each test compound, the dose at which 50% of the maximal inhibition of cAMP level is observed ($EC_{50}$, expressed in the Table as $pEC_{50}=-\log(EC_{50})$ values) and the level of inhibition reached with 10 µM of the test compound compared to WIN55212-2 (for hCB2) was calculated.

TABLE D.1 pEC50 values for CB-2 agonism

| Co. No. | CB2 pEC50 |
|---|---|
| 1 | 8.07 |
| 3 | 7.81 |
| 5 | 8.62 |
| 6 | 7.72 |
| 7 | 7.77 |
| 8 | 7.64 |
| 9 | 5.80 |
| 10 | 7.66 |
| 11 | 7.69 |
| 12 | 6.80 |
| 13 | 8.06 |
| 15 | 8.00 |
| 16 | 8.68 |
| 17 | 9.10 |
| 18 | 8.20 |
| 19 | 6.84 |
| 20 | 7.59 |
| 21 | 8.27 |
| 22 | 8.15 |
| 23 | 8.43 |
| 24 | 8.03 |
| 25 | 7.91 |
| 26 | 8.05 |
| 27 | 7.21 |
| 28 | 7.63 |
| 29 | 7.56 |
| 30 | 7.30 |
| 31 | 8.07 |
| 32 | 8.89 |
| 33 | 8.35 |
| 34 | 8.41 |
| 35 | 8.49 |
| 36 | 8.66 |
| 37 | 8.88 |
| 38 | 8.59 |
| 39 | 8.15 |
| 40 | 8.23 |
| 41 | 8.93 |
| 42 | 8.26 |
| 43 | 8.06 |
| 46 | 7.27 |
| 47 | 6.02 |
| 48 | 7.16 |
| 49 | 8.13 |
| 50 | 8.11 |
| 51 | 9.10 |
| 52 | 8.40 |
| 53 | 8.53 |
| 54 | 8.64 |
| 55 | 7.03 |
| 56 | 8.47 |
| 57 | 8.80 |
| 58 | 8.07 |
| 59 | 8.56 |
| 60 | 8.46 |
| 61 | 8.60 |
| 62 | 8.28 |
| 63 | 7.81 |
| 64 | 7.89 |
| 65 | 8.76 |
| 66 | 8.65 |
| 67 | 8.56 |
| 68 | 8.53 |
| 69 | 8.23 |
| 70 | 10.06 |
| 71 | 8.13 |

TABLE D.1-continued pEC50 values for CB-2 agonism

| Co. No. | CB2 pEC50 |
|---------|-----------|
| 72      | 7.89      |
| 73*     | 8.63      |
| 76      | 9.11      |
| 79      | 8.23      |
| 80      | ~7.33     |
| 82      | 8.66      |
| 84      | 8.48      |
| 86      | 8.27      |
| 87      | ~8        |
| 88      | 9.27      |
| 89      | ~9.96     |
| 90      | 9.13      |
| 91      | ~9.08     |
| 92      | 8.39      |
| 93      | ~9.62     |
| 94      | ~8.48     |
| 95      | ~8.57     |
| 96      | 8.45      |
| 97      | 8.32      |
| 98      | 8.34      |
| 100     | 8.63      |
| 101     | ~9.29     |
| 102     | ~8.46     |
| 103     | ~8.42     |
| 104     | ~7.63     |
| 105     | ~8.89     |
| 106     | ~7.64     |
| 107     | ~8.13     |
| 108     | ~7.86     |
| 109     | ~8.06     |
| 110     | ~8.0      |
| 111     | ~7.78     |
| 112     | ~7.78     |
| 113     | ~8.6      |
| 114     | ~8.38     |
| 115     | ~8.08     |
| 116     | ~7.35     |

*Co. No. (73) was tested as its HCl salt

D.2 Comparative Data

CB1 related undesired side-effects such as lowering of body temperature, flat body posture, and mydriasis were measured for a number of compounds of the present invention and a number of compounds covered by reference WO-2006/048754. For both sets of compounds the LAD (Lowest Acceptable Dose) at which an effect on body temperature, i.e. lowering, was observed in more than half of the treated animals was determined. Data are listed in Table D-3.

TABLE D-2 structures of compounds of present application

| Compounds of present invention | Compounds of WO-2006/048754 |
|---|---|
| 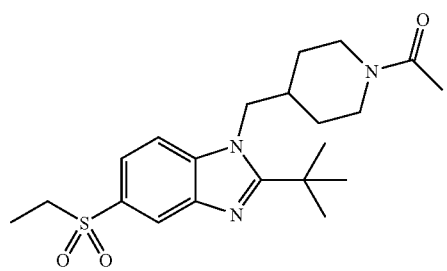<br>Co. No. 1 | 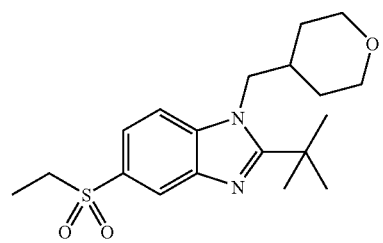<br>Co. No. A |
| 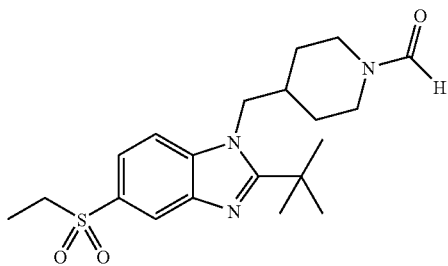<br>Co. No. 28 | 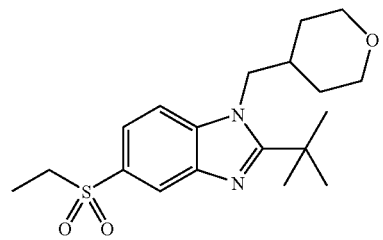<br>Co. No. A |
| 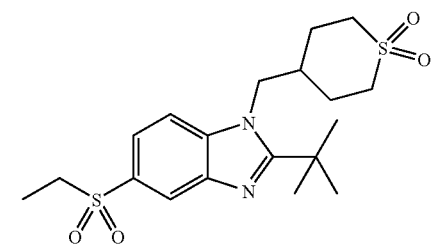 | |

TABLE D-2-continued
structures of compounds of present application
| Compounds of present invention | Compounds of WO-2006/048754 |
|---|---|
| Co. No. 29 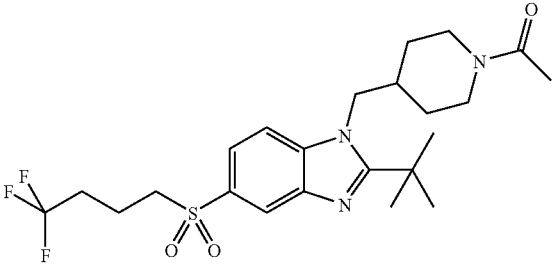 | Co. No. A 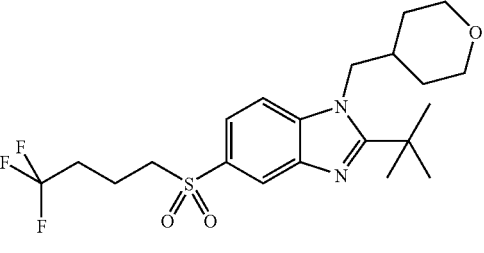 |
| Co. No. 3 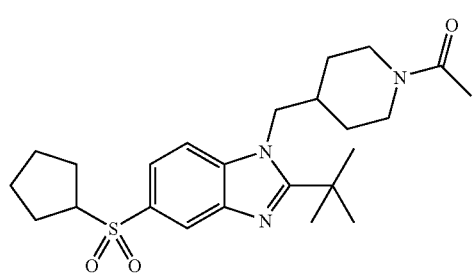 | Co. No. B 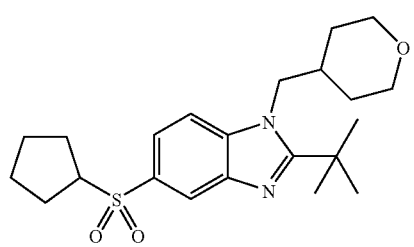 |
| Co. No. 35 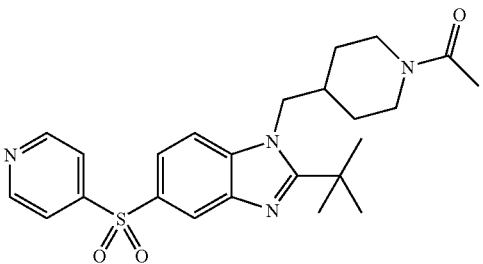 | Co. No. C 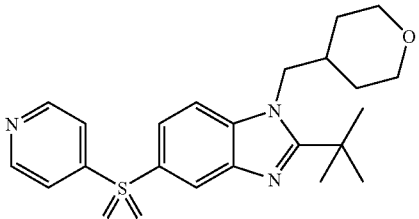 |
| Co. No. 34 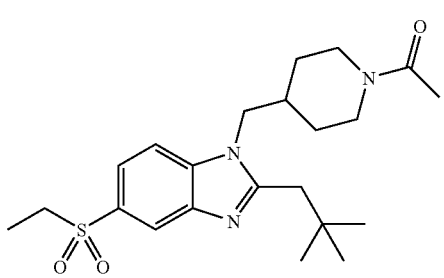 | Co. No. D 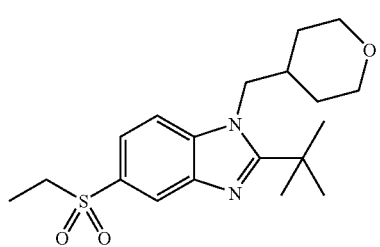 |
| Co. No. 46  | Co. No. F  |
TABLE D-3
comparitive data for body temperature lowering
| Present invention | LAD | Ref. compounds | LAD |
|---|---|---|---|
| Co. No. 1 | >40 mg/kg | Co. No. A | 10 mg/kg |
| Co. No. 28 | >40 mg/kg | Co. No. A | 10 mg/kg |
| Co. No. 29 | >40 mg/kg | Co. No. A | 10 mg/kg |
| Co. No. 3 | >40 mg/kg | Co. No. B | 10 mg/kg |

TABLE D-3-continued comparitive data for body temperature lowering

| Present invention | LAD | Ref. compounds | LAD |
|---|---|---|---|
| Co. No. 35 | >40 mg/kg | Co. No. C | 5 mg/kg |
| Co. No. 34 | >40 mg/kg | Co. No. D | 10 mg/kg |
| Co. No. 46 | >40 mg/kg | Co. No. F | 10 mg/kg |

The invention claimed is:
1. Compound of formula (I)

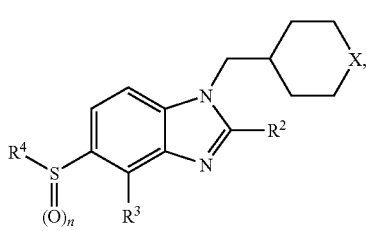

including any stereochemically isomeric form thereof, wherein
n is an integer 0, 1 or 2;
X is SO, $SO_2$ or N—(CO)—$R^1$;
$R^1$ is hydrogen;
  $C_{1-6}$alkyl;
  $C_{1-6}$alkyloxy;
  $C_{1-4}$alkyloxy$C_{1-4}$alkyl; or
  polyhalo$C_{1-6}$alkyl;
$R^2$ is $C_{1-6}$alkyl;
$R^3$ is hydrogen, halo, $C_{1-4}$alkyl, $C_{1-4}$alkyloxy, trifluoromethyl or cyano;
$R^4$ is $C_{1-8}$alkyl;
  $C_{1-8}$alkyl substituted with $C_{3-8}$cycloalkyl;
  polyhalo$C_{1-8}$alkyl;
  $C_{1-8}$alkyl substituted with 1, 2 or 3 substituents each independently selected from hydroxy, $C_{1-4}$alkyloxy, polyhalo$C_{1-4}$alkyloxy, cyano, nitro, tetrahydropyranyl, tetrahydrofuranyl, oxetanyl, aryl, or heteroaryl;
  $C_{3-8}$cycloalkyl;
  $C_{3-8}$cycloalkyl substituted with 1, 2 or 3 substituents each independently selected from hydroxy, $C_{1-4}$alkyloxy, polyhalo$C_{1-4}$alkyloxy, cyano, nitro, tetrahydropyranyl, tetrahydrofuranyl, oxetanyl, aryl, or heteroaryl;
  tetrahydropyranyl, tetrahydrofuranyl, oxetanyl
  aryl; or
  heteroaryl;
aryl is phenyl; or phenyl substituted with 1, 2 or 3 substituents each independently selected from halo, hydroxy, $C_{1-4}$alkyl, polyhalo$C_{1-4}$alkyl, $C_{1-4}$alkyloxy, polyhalo$C_{1-4}$alkyloxy, cyano, nitro, $NR^5R^6$, $R^7$-carbonyl, $R^7$—$SO_2$—, or $C_{1-4}$alkyl substituted with hydroxy, $NR^5R^6$, $R^7$-carbonyl or $R^7$—$SO_2$—;
heteroaryl is selected from from furanyl, thiophenyl, pyrrolyl, pyrazolyl, imidazolyl, isoxazolyl, thiazolyl, triazolyl, tetrazolyl, isothiazolyl, thiadiazolyl, oxadiazolyl, pyridinyl, pyridazinyl, pyrimidinyl, or pyrazinyl;
wherein $R^5$ and $R^6$ are independently from one another selected from hydrogen, $C_{1-4}$alkyl, polyhalo$C_{1-4}$alkyl, aminosulfonyl, or $C_{1-8}$alkylsulfonyl; or $R^7$-carbonyl, or;
wherein $R^5$ and $R^6$ are taken together with the nitrogen atom bearing $R^5$ and $R^6$ may form a pyrrolidinyl, piperidinyl, piperazinyl or morpholinyl ring; and wherein $R^7$ is $C_{1-4}$alkyl, hydroxy, amino, mono- or di-($C_{1-4}$alkyl)amino, (hydroxy$C_{1-4}$alkyl)amino, ($C_{1-4}$alkyloxy$C_{1-4}$alkyl)amino, di($C_{1-4}$alkyl)amino$C_{1-4}$alkyl, pyrrolidinyl, piperidinyl, morpholinyl, or N-methylpiperazinyl;
or a pharmaceutically acceptable acid addition salt thereof.
2. A compound as claimed in claim 1 wherein X is $SO_2$.
3. A compound as claimed in claim 1 wherein X is N—(CO)—$R^1$.
4. A pharmaceutical composition comprising a pharmaceutically acceptable carrier and a therapeutically active amount of a compound of formula (I)

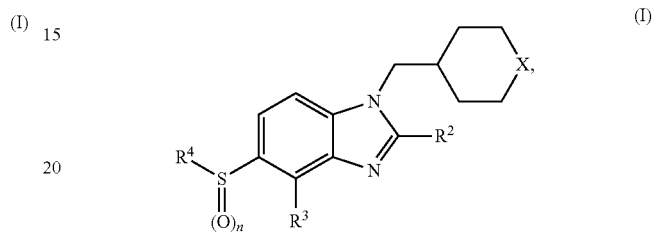

including any stereochemically isomeric form thereof, wherein
n is an integer 0, 1 or 2;
X is SO, $SO_2$ or N—(CO)—$R^1$;
$R^1$ is hydrogen;
  $C_{1-6}$alkyl;
  $C_{1-6}$alkyloxy;
  $C_{1-4}$alkyloxy$C_{1-4}$alkyl; or
  polyhalo$C_{1-6}$alkyl;
$R^2$ is $C_{1-6}$alkyl;
$R^3$ is hydrogen, halo, $C_{1-4}$alkyl, $C_{1-4}$alkyloxy, trifluoromethyl or cyano;
$R^4$ is $C_{1-8}$alkyl;
  $C_{1-8}$alkyl substituted with $C_{3-8}$cycloalkyl;
  polyhalo$C_{1-8}$alkyl;
  $C_{1-8}$alkyl substituted with 1, 2 or 3 substituents each independently selected from hydroxy, $C_{1-4}$alkyloxy, polyhalo$C_{1-4}$alkyloxy, cyano, nitro, tetrahydropyranyl, tetrahydrofuranyl, oxetanyl, aryl, or heteroaryl;
  $C_{3-8}$cycloalkyl;
  $C_{3-8}$cycloalkyl substituted with 1, 2 or 3 substituents each independently selected from hydroxy, $C_{1-4}$alkyloxy, polyhalo$C_{1-4}$alkyloxy, cyano, nitro, tetrahydropyranyl, tetrahydrofuranyl, oxetanyl, aryl, or heteroaryl;
  tetrahydropyranyl, tetrahydrofuranyl, oxetanyl
  aryl; or
  heteroaryl;
aryl is phenyl; or phenyl substituted with 1, 2 or 3 substituents each independently selected from halo, hydroxy, $C_{1-4}$alkyl, polyhalo$C_{1-4}$alkyl, $C_{1-4}$alkyloxy, polyhalo$C_{1-4}$alkyloxy, cyano, nitro, $NR^5R^6$, $R^7$-carbonyl, $R^7$—$SO_2$—, or $C_{1-4}$alkyl substituted with hydroxy, $NR^5R^6$, $R^7$-carbonyl or $R^7$—$SO_2$—;
heteroaryl is selected from from furanyl, thiophenyl, pyrrolyl, pyrazolyl, imidazolyl, isoxazolyl, thiazolyl, triazolyl, tetrazolyl, isothiazolyl, thiadiazolyl, oxadiazolyl, pyridinyl, pyridazinyl, pyrimidinyl, or pyrazinyl;
wherein $R^5$ and $R^6$ are independently from one another selected from hydrogen, $C_{1-4}$alkyl, polyhalo$C_{1-4}$alkyl, aminosulfonyl, or $C_{1-8}$alkylsulfonyl; or $R^7$-carbonyl, or;
wherein $R^5$ and $R^6$ are taken together with the nitrogen atom bearing $R^5$ and $R^6$ may form a pyrrolidinyl, piperidinyl, piperazinyl or morpholinyl ring; and wherein R$^7$ is C$_{1-4}$alkyl, hydroxy, amino, mono- or di-(C$_{1-4}$alkyl)amino, (hydroxyC$_{1-4}$alkyl)amino, (C$_{1-4}$alkyloxyC$_{1-4}$alkyl)amino, di(C$_{1-4}$alkyl)aminoC$_{1-4}$alkyl, pyrrolidinyl, piperidinyl, morpholinyl, or N-methylpiperazinyl;

or a pharmaceutically acceptable acid addition salt thereof.

5. A process for preparing a compound of formula (I-a), defined as a compound of formula (I) as claimed in claim 1 wherein n is 0, by reacting an intermediate (II) with an intermediate (III), wherein L is a leaving group in the presence of a suitable base in a reaction-inert solvent;

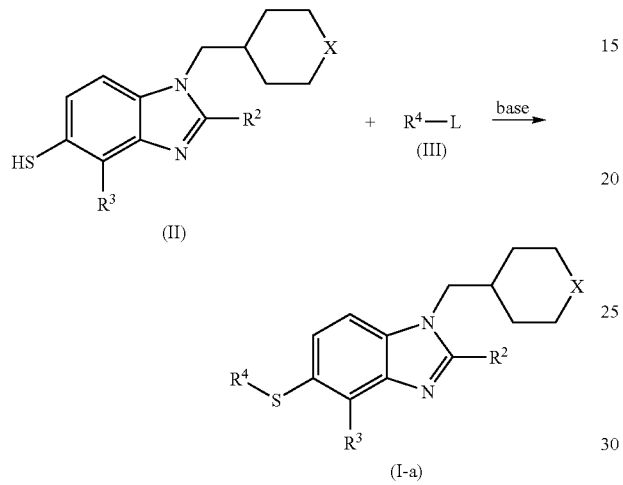

wherein R$^2$, R$^3$ and R$^4$ are defined as in claim 1; or
a compound of formula (I-a) is converted into a pharmaceutically acceptable acid addition salt, or an acid addition salt of a compound of formula (I-a) is converted into a free base form with alkali; and, optionally, preparing stereochemically isomeric forms thereof.

6. A process for preparing a compound of formula (I-b), defined as a compound of formula (I) as claimed in claim 1 wherein n is 1, by S-oxidizing a compound of formula (I-a), wherein X, R$^2$, R$^3$ and R$^4$ are as defined in claim 1, with an oxidizing agent;

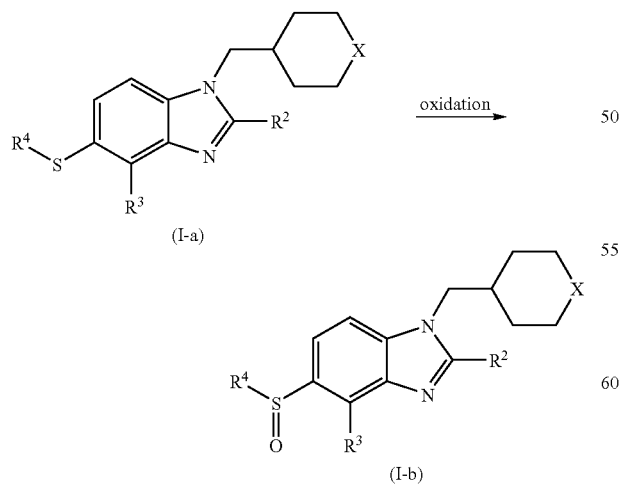

or; a compound of formula (I-b) is converted into a pharmaceutically acceptable acid addition salt, or an acid addition salt of a compound of formula (I-b) is converted into a free base form with alkali; and, optionally, preparing stereochemically isomeric forms thereof.

7. A process for preparing a compound of formula (I-c), defined as a compound of formula (I) as claimed in claim 1 wherein n is 1, by S-oxidizing a compound of formula (I-a), wherein X, R$^2$, R$^3$ and R$^4$ are as defined in claim 1, with an oxidizing agent;

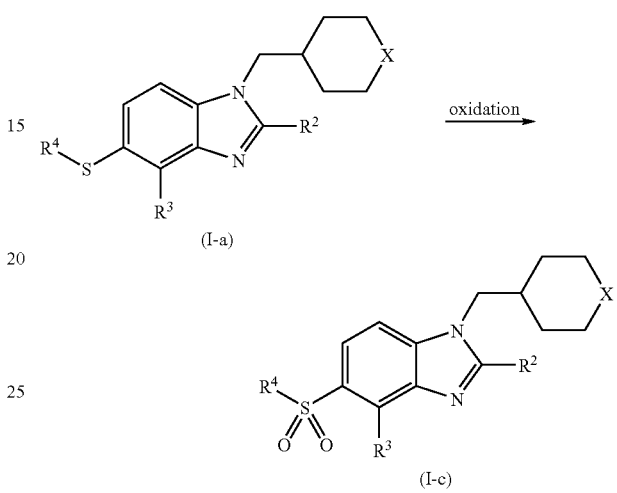

or; a compound of formula (I-c) is converted into a pharmaceutically acceptable acid addition salt, or an acid addition salt of a compound of formula (I-c) is converted into a free base form with alkali; and, preparing stereochemically isomeric forms thereof.

8. A process for preparing a compound of formula (I-d), wherein
n is an integer 0, 1 or 2;
R$^1$ is hydrogen;
  C$_{1-6}$alkyl;
  C$_{1-6}$alkyloxy;
  C$_{1-4}$alkyloxyC$_{1-4}$alkyl; or
  polyhaloC$_{1-6}$alkyl;
R$^2$ is C$_{1-6}$alkyl;
R$^3$ is hydrogen, halo, C$_{1-4}$alkyl, C$_{1-4}$alkyloxy, trifluoromethyl or cyano;
R$^4$ is C$_{1-8}$alkyl;
  C$_{1-8}$alkyl substituted with C$_{3-8}$cycloalkyl;
  polyhaloC$_{1-8}$alkyl;
  C$_{1-8}$alkyl substituted with 1, 2 or 3 substituents each independently selected from hydroxy, C$_{1-4}$alkyloxy, polyhaloC$_{1-4}$alkyloxy, cyano, nitro, tetrahydropyranyl, tetrahydrofuranyl, oxetanyl, aryl, or heteroaryl;
  C$_{3-8}$cycloalkyl;
  C$_{3-8}$cycloalkyl substituted with 1, 2 or 3 substituents each independently selected from hydroxy, C$_{1-4}$alkyloxy, polyhaloC$_{1-4}$alkyloxy, cyano, nitro, tetrahydropyranyl, tetrahydrofuranyl, oxetanyl, aryl, or heteroaryl;
  tetrahydropyranyl, tetrahydrofuranyl, oxetanyl
  aryl; or
  heteroaryl;
aryl is phenyl; or phenyl substituted with 1, 2 or 3 substituents each independently selected from halo, hydroxy, C$_{1-4}$alkyl, polyhaloC$_{1-4}$alkyl, C$_{1-4}$alkyloxy, polyhaloC$_{1-4}$alkyloxy, cyano, nitro, NR$^5$R$^6$, R$^7$-carbonyl, $R^7$—$SO_2$—, or $C_{1-4}$alkyl substituted with hydroxy, $NR^5R^6$, $R^7$-carbonyl or $R^7$—$SO_2$—;

heteroaryl is selected from from furanyl, thiophenyl, pyrrolyl, pyrazolyl, imidazolyl, isoxazolyl, thiazolyl, triazolyl, tetrazolyl, isothiazolyl, thiadiazolyl, oxadiazolyl, pyridinyl, pyridazinyl, pyrimidinyl, or pyrazinyl;

said process comprising N-alkylating an intermediate (V) with an intermediate (VI), wherein W is an appropriate leaving group in a reaction inert solvent,

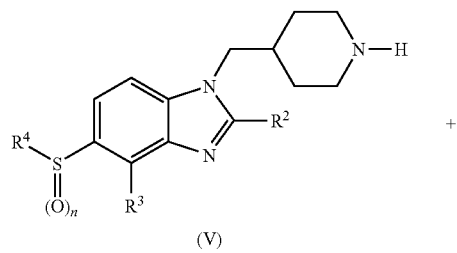

(V)

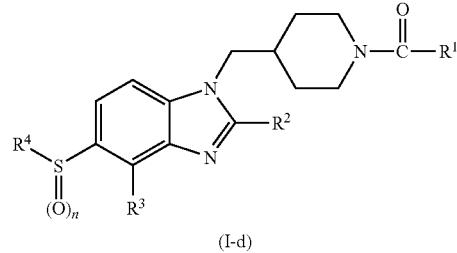

(VI)

(I-d)

or; a compound of formula (I-d) is converted into a pharmaceutically acceptable acid addition salt, or an acid addition salt of a compound of formula (I-d) is converted into a free base form with alkali; and, preparing stereochemically isomeric forms thereof.

* * * * *